(12) United States Patent
Sosnovik et al.

(10) Patent No.: US 11,779,661 B2
(45) Date of Patent: Oct. 10, 2023

(54) THERANOSTIC NUCLEIC ACID BINDING FLUORESCENT NANOPROBES AND USES THEREOF

(71) Applicant: The General Hospital Corporation, Boston, MA (US)

(72) Inventors: David Sosnovik, Newton, MA (US); Lee Josephson, Reading, MA (US); Howard Chen, Milton, MA (US)

(73) Assignee: The General Hospital Corporation, Boston, MA (US)

( * ) Notice: Subject to any disclaimer, the term of this patent is extended or adjusted under 35 U.S.C. 154(b) by 694 days.

(21) Appl. No.: 16/348,572

(22) PCT Filed: Nov. 8, 2017

(86) PCT No.: PCT/US2017/060552
§ 371 (c)(1),
(2) Date: May 9, 2019

(87) PCT Pub. No.: WO2018/089434
PCT Pub. Date: May 17, 2018

(65) Prior Publication Data
US 2019/0269802 A1 Sep. 5, 2019

Related U.S. Application Data

(60) Provisional application No. 62/420,318, filed on Nov. 10, 2016.

(51) Int. Cl.
| | | |
|---|---|---|
| *A61K 49/00* | (2006.01) | |
| *A61K 47/61* | (2017.01) | |
| *A61K 51/04* | (2006.01) | |
| *A61K 47/69* | (2017.01) | |
| *A61K 49/10* | (2006.01) | |
| *C07D 221/12* | (2006.01) | |
| *C07D 417/06* | (2006.01) | |
| *C07D 413/06* | (2006.01) | |

(52) U.S. Cl.
CPC .......... *A61K 49/0054* (2013.01); *A61K 47/61* (2017.08); *A61K 47/6929* (2017.08); *A61K 49/0021* (2013.01); *A61K 49/0032* (2013.01); *A61K 49/0052* (2013.01); *A61K 49/10* (2013.01); *A61K 51/0491* (2013.01); *A61K 51/0497* (2013.01); *C07D 221/12* (2013.01); *C07D 413/06* (2013.01); *C07D 417/06* (2013.01)

(58) Field of Classification Search
CPC ............ A61K 49/0054; A61K 49/0052; A61K 49/0021; A61K 47/6929
See application file for complete search history.

(56) References Cited

U.S. PATENT DOCUMENTS

| | | | |
|---|---|---|---|
| 5,262,176 A * | 11/1993 | Palmacci | ................. C08J 9/144 428/407 |
| 2002/0177136 A1* | 11/2002 | McBranch | ......... G01N 21/6428 534/727 |
| 2005/0249668 A1 | 11/2005 | Weissleder et al. | |
| 2006/0275775 A1 | 12/2006 | Weissleder et al. | |
| 2012/0121509 A1 | 5/2012 | Josephson et al. | |
| 2015/0184227 A1 | 7/2015 | Hamasaki et al. | |
| 2016/0243254 A1 | 8/2016 | Artzi et al. | |

FOREIGN PATENT DOCUMENTS

WO WO 2010/141833 12/2010

OTHER PUBLICATIONS

Sirlin et al. "Gadolinium-DTPA-Dextran: A Macromolecular MR Blood Pool Contrast Agent", Academic Radiology, vol. 11, No. 12, Dec. 2004. This new rejection was necessitated by amendment (Year: 2004).*
Barrat et al., "Treatment of lupus-prone mice with a dual inhibitor of TLR7 and TLR9 leads to reduction of autoantibody production and amelioration of disease symptoms," European Journal of Immunology, Dec. 2007, 37(12):3582-6.
Berge et al., "Pharmaceutical salts," Journal of Pharmaceutical Sciences, Jan. 1, 1977, 66(1):1-9.
Blanckmeister et al., "Macrophage activation by cross-linked dextran," Journal of Leukocyte Biology, Feb. 1985, 37(2):209-19.
Cabrera-Fuentes et al., "RNase1 prevents the damaging interplay between extracellular RNA and tumour necrosis factor-α in cardiac ischaemia/reperfusion injury," Thrombosis and Haemostasis, 112(12):1110-9.
Cavassani et al., "TLR3 is an endogenous sensor of tissue necrosis during acute inflammatory events," Journal of Experimental Medicine, Oct. 27, 2008, 205(11):2609-21.
Chen et al., "Role of Extracellular RNA and TLR 3-Trif Signaling in Myocardial Ischemia-Reperfusion Injury," Journal of the American Heart Association. Jan. 3, 2014, 3(1):e000683, 30 pages.
Cho et al., "Fluorochrome-functionalized nanoparticles for imaging DNA in biological systems," ACS Nano, Feb. 7, 2013, 7(3):2032-41.
Cho et al., "Imaging DNA with Fluorochrome Bearing Metals," Inorganic Chemistry, May 6, 2013, 52(21):12216-22.
Coutinho et al., "Molecular Basis of B-Cell Activation: I. Mitogenicity of Native and Substituted Dextrans," Scandinavian Journal of Immunology, Jun. 1974, 3(3):321-38.
Dreher et al., "Tumor vascular permeability, accumulation, and penetration of macromolecular drug carriers," Journal of the National Cancer Institute, Mar. 1, 2006, 98(5):335-44.
Duplancic et al., "Pentadecapeptide BPC 157 and anaphylactoid reaction in rats and mice after intravenous dextran and white egg administration," European Journal of Pharmacology, Mar. 15, 2014, 727:75-9.
Feng et al., "Cardiac RNA induces inflammatory responses in cardiomyocytes and immune cells via Toll-like receptor 7 signaling," Journal of Biological Chemistry, Oct. 30, 2015, 290(44):26688-98.

(Continued)

Primary Examiner — James W Rogers
(74) Attorney, Agent, or Firm — Fish & Richardson P.C.

(57) ABSTRACT

The present disclosure provides nucleic acid binding nanoprobes having one or more fluorochromes and a polymer, where each of the fluorochromes is connected to the polymer, and methods of using the same.

14 Claims, 13 Drawing Sheets

(56) References Cited

OTHER PUBLICATIONS

Fuchs et al., "Extracellular DNA traps promote thrombosis," Proceedings of the National Academy of Sciences, Sep. 7, 2010, 107(36):15880-5.
Garanger et al., "A DNA-binding Gd chelate for the detection of cell death by MRI," Chemical Communications, Jun. 11, 2009, (29):4444-6.
Heidt et al., "Differential contribution of monocytes to heart macrophages in steady-state and after myocardial infarction," Circulation Research, Jul. 7, 2014, 115(2):284-95.
Holl et al., "Nucleic acid scavenging polymers inhibit extracellular DNA-mediated innate immune activation without inhibiting antiviral responses," PloS one, Jul. 23, 2013, 8(7):e69413, 10 pages.
Huang et al., "Molecular MRI of acute necrosis with a novel DNA-binding gadolinium chelate: kinetics of cell death and clearance in infarcted myocardium," Circulation: Cardiovascular Imaging, Nov. 2011, 4(6):729-37.
Jain et al., "Nucleic acid scavengers inhibit thrombosis without increasing bleeding," Proceedings of the National Academy of Sciences, Aug. 7, 2012, 109(32):12938-43.
Kumar et al., "A time domain fluorescence tomography system for small animal imaging. IEEE transactions on medical imaging," Feb. 8, 2008, 27(8):1152-63.
Lee et al., "PET/MRI of inflammation in myocardial infarction," Journal of the American College of Cardiology, Jan. 10, 2012, 59(2):153-63.
Leuschner et al., "Therapeutic siRNA silencing in inflammatory monocytes in mice," Nature Biotechnology, Nov. 2011, 29(11):1005-10.
Montet-Abou et al., "In vivo labelling of resting monocytes in the reticuloendothelial system with fluorescent iron oxide nanoparticles prior to injury reveals that they are mobilized to infarcted myocardium," European Heart Journal, Dec. 19, 2009, 31(11):1410-20.
Nygren et al., "The interactions between the fluorescent dye thiazole orange and DNA," Biopolymers: Original Research on Biomolecules, Jul. 1998, 46(1):39-51.
PCT International Preliminary Report on Patentability dated May 14, 2019 in International Application No. PCT/US2017/060552, 8 pages.
Plitas et al., "Toll-like receptor 9 inhibition reduces mortality in polymicrobial sepsis," Journal of Experimental Medicine, Jun. 9, 2008, 205(6):1277-83.
Shak et al., "Recombinant human DNase I reduces the viscosity of cystic fibrosis sputum," Proceedings of the National Academy of Sciences, Dec. 1, 1990, 87(23):9188-92.
Stearns et al., "The inhibition of anti-DNA binding to DNA by nucleic acid binding polymers," PloS one, Jul. 11, 2012, 7(7):e40862, Stearns.
Takakura et al., "Macromolecular carrier systems for targeted drug delivery; pharmacokinetic considerations on biodistribution," Pharmaceutical Research, Jun. 1, 1996, 13(6):820-31.
Vogel et al., "Acute DNase1 treatment improves left ventricular remodeling after myocardial infarction by disruption of free chromatin," Basic Research in Cardiology, Mar. 1, 2015, 110(2):15, 15 pages.
International Search Report and Written Opinion dated Jan. 4, 2018 in International Application No. PCT/US2017/060552, 14 pgs.
Vasanawala et al., "Safety and Technique of Femmoxytol Administration for MRI," Magn Reson Med., May 2016, 75(5):2107-2111.

\* cited by examiner

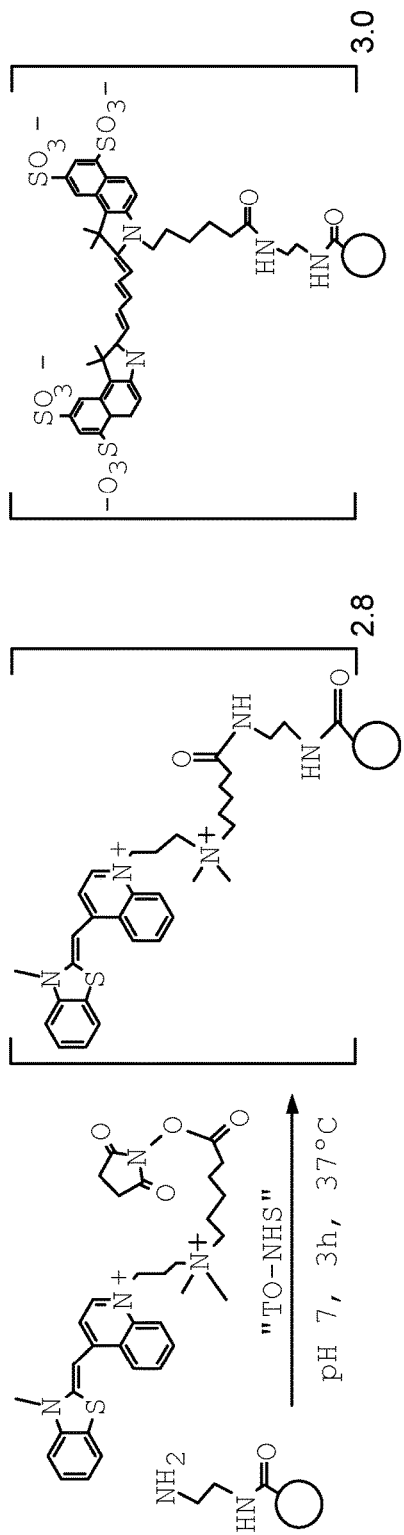
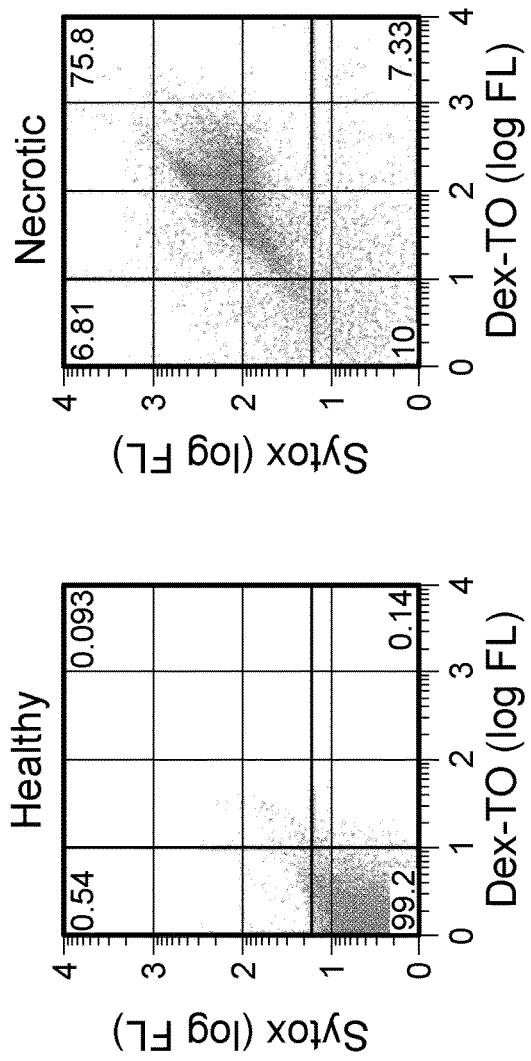
FIG. 1A  FIG. 1B  FIG. 1C  FIG. 1D

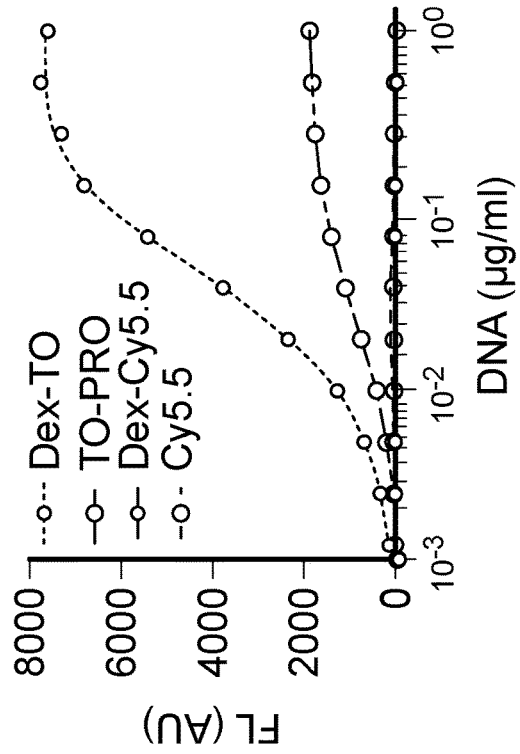
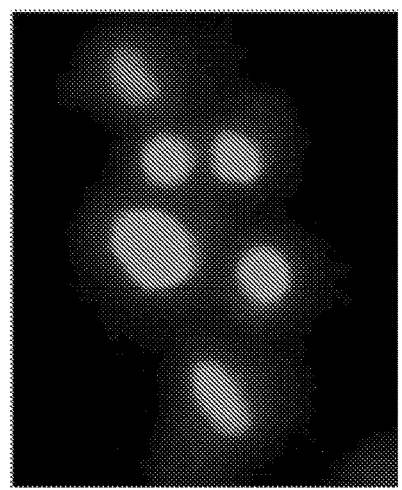
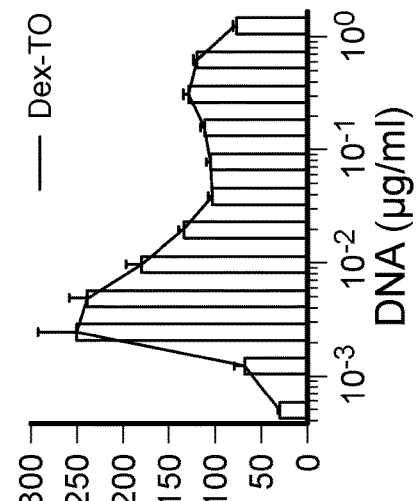
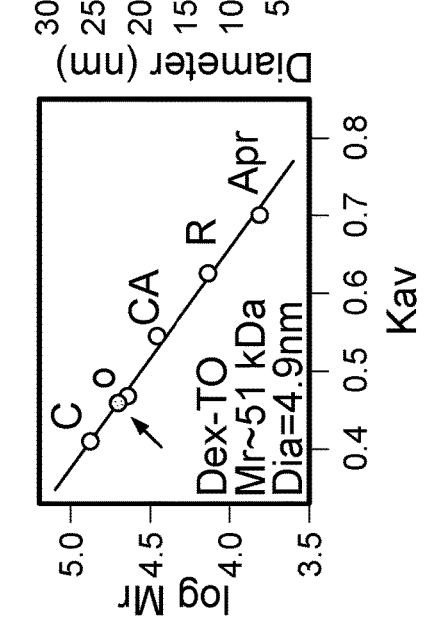
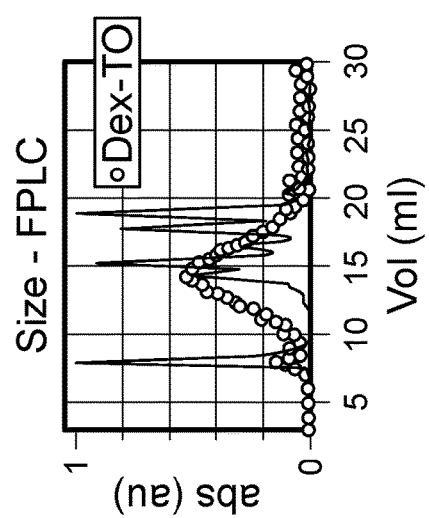

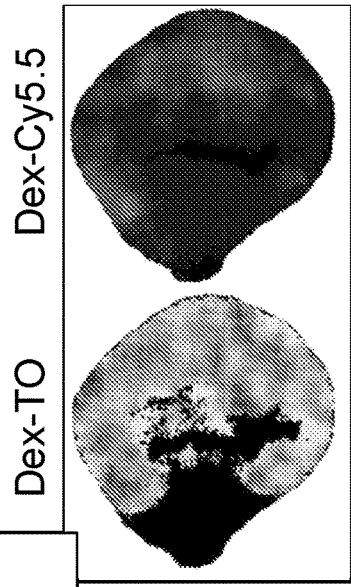
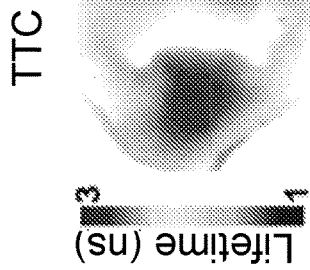
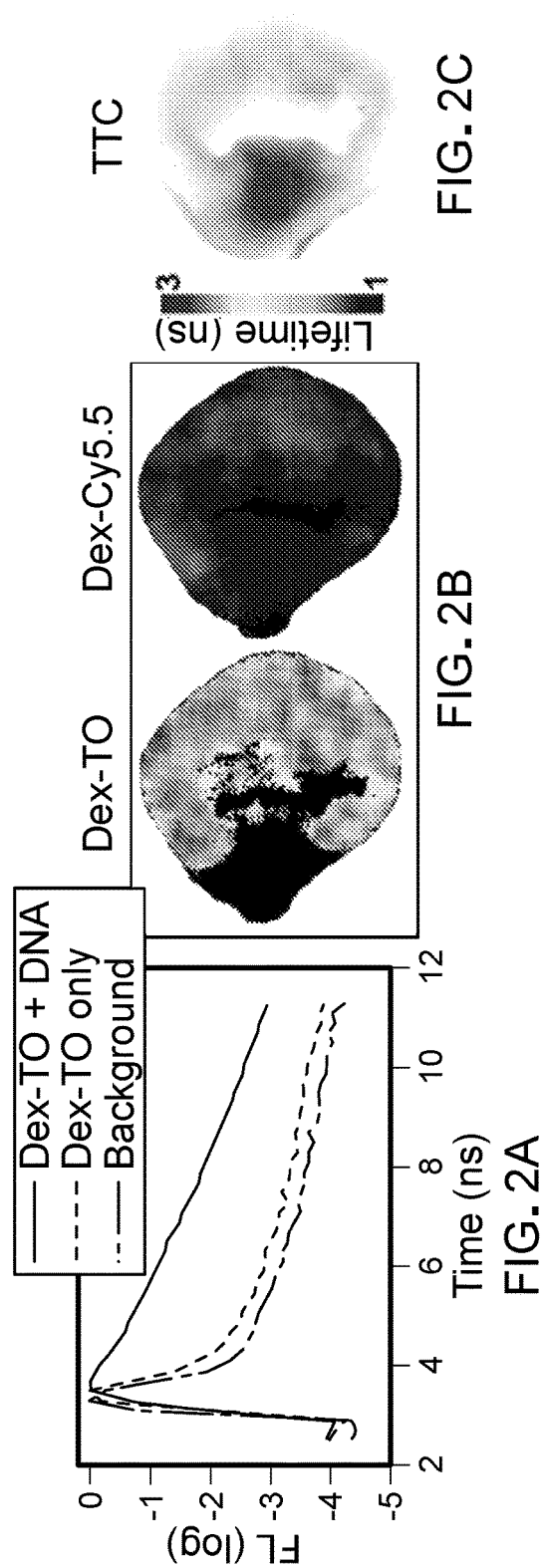
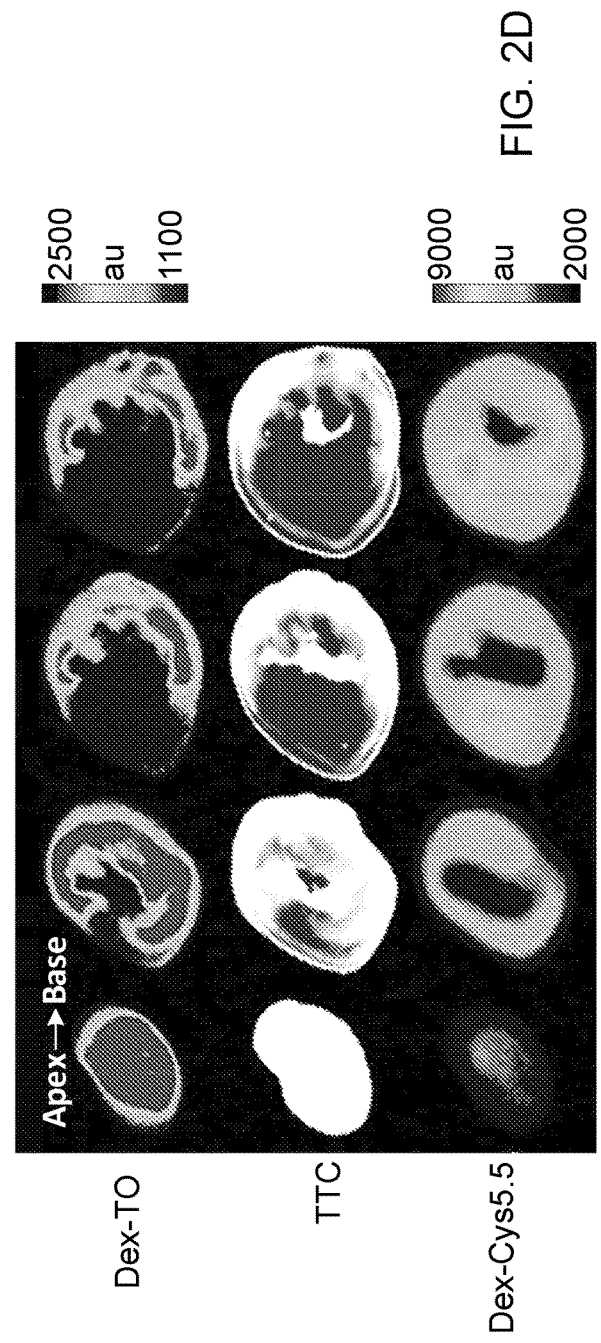

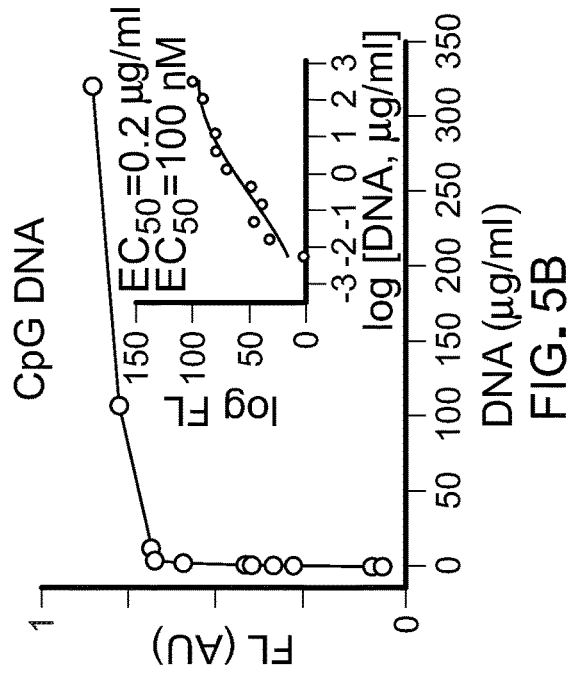
FIG. 5A
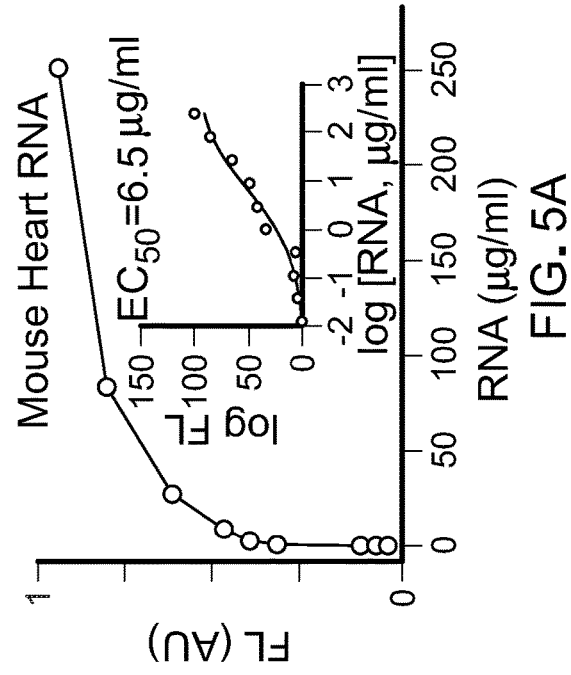
FIG. 5B
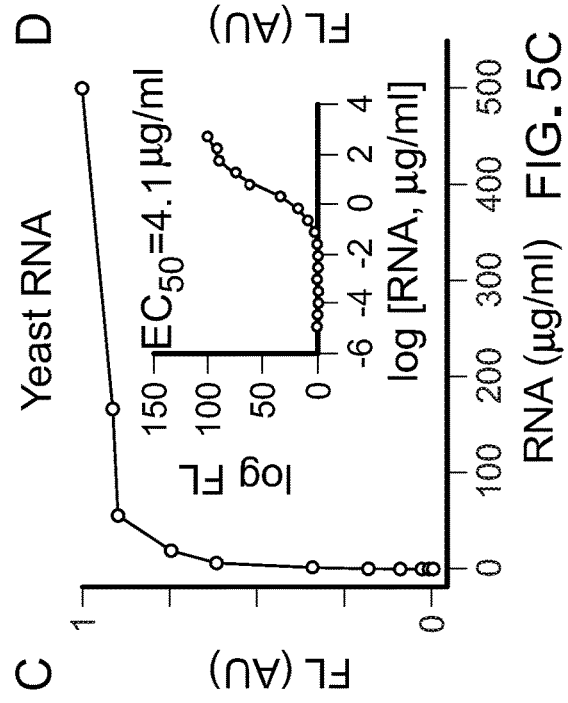
FIG. 5C
FIG. 5D

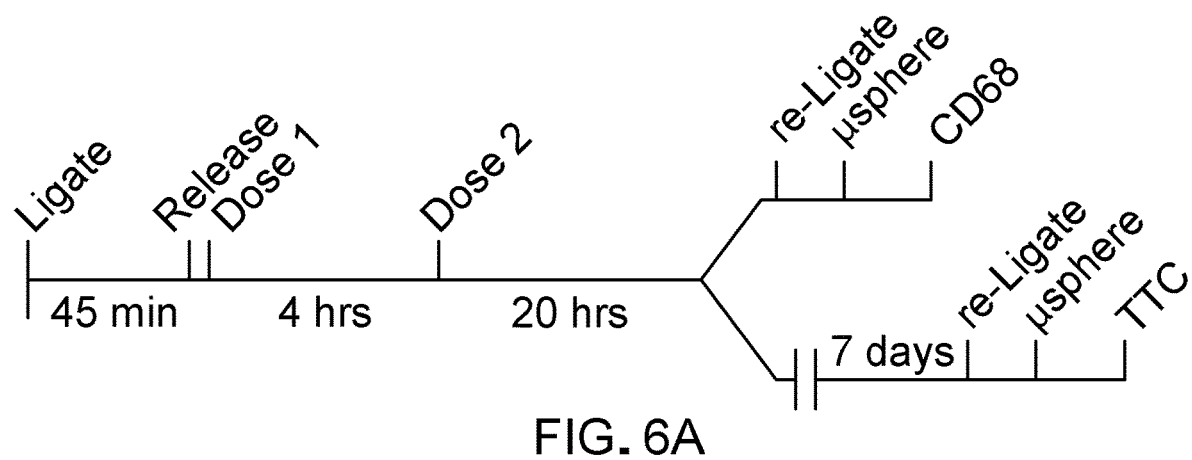
FIG. 6A
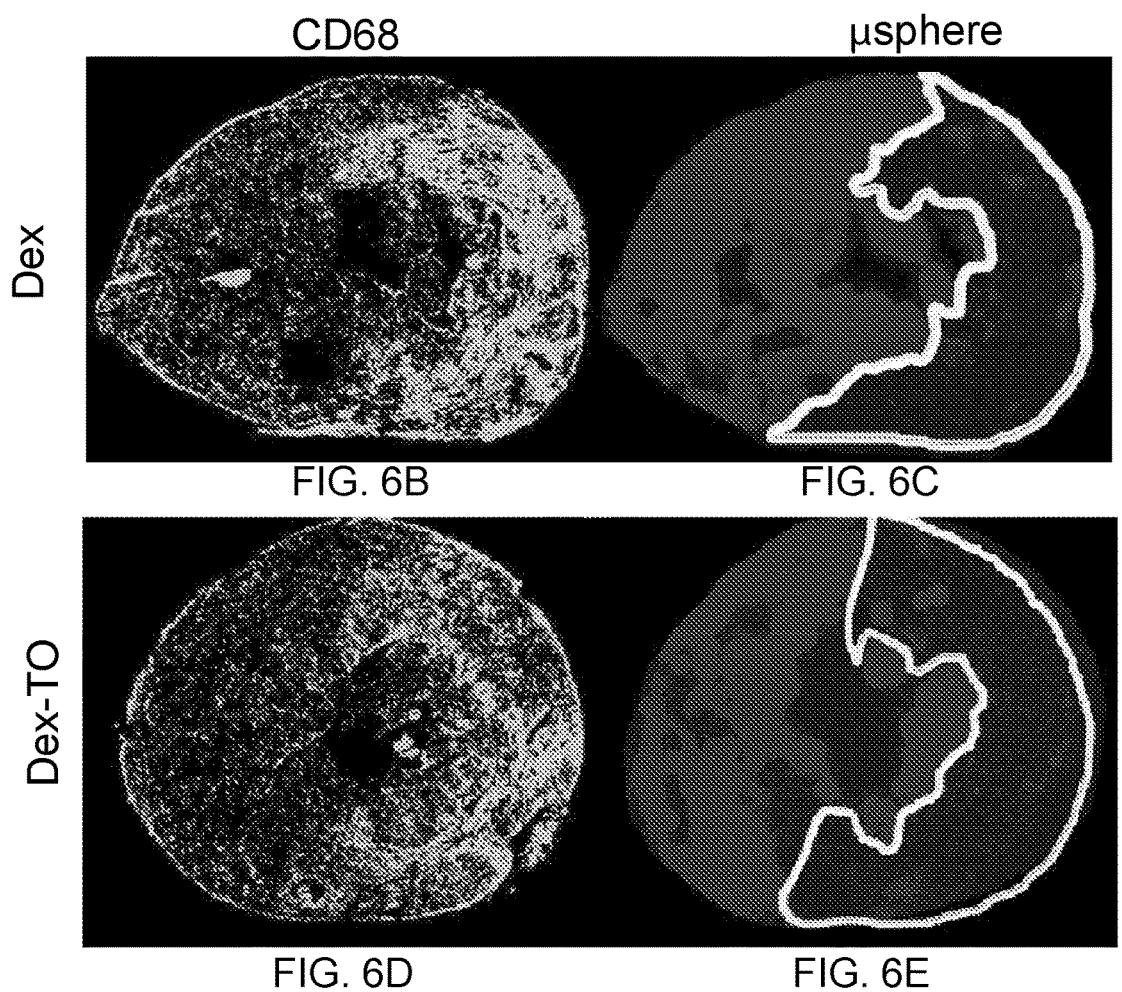
FIG. 6B  FIG. 6C
FIG. 6D  FIG. 6E

THERANOSTIC NUCLEIC ACID BINDING FLUORESCENT NANOPROBES AND USES THEREOF

CROSS-REFERENCE TO RELATED APPLICATIONS

This application is a national stage application under 35 USC § 371 of International Application No. PCT/US2017/060552, filed on Nov. 8, 2017, which claims priority to U.S. Provisional Application Ser. No. 62/420,318, filed on Nov. 10, 2016, the contents of which are hereby incorporated by reference in their entirety.

STATEMENT REGARDING FEDERALLY SPONSORED RESEARCH OR DEVELOPMENT

The present invention was made with government support under Grant No. R01-EB011996 awarded by the National Institutes of Health. The United States Government has certain rights in the invention.

TECHNICAL FIELD

The present disclosure describes the nanoprobes that includes one or more vital fluorochromes and a polymer, where each of the vital fluorochrome is connected to the polymer by a linker.

BACKGROUND OF THE INVENTION

Nucleic acids (NAs), including DNA and RNA, are stimulants of the immune response. Stimulation of the immune system by NAs can be either in response to injury, where endogenous NAs are released, or due to infection, where the immune system is exposed to the NAs of the invading micro-organism. In both scenarios, the circulating NAs provoke an exuberant inflammatory response, which ultimately worsens the degree of tissue damage. Thus, there exists a need for compositions that bind to NAs and limit the damage from injury and infection.

SUMMARY OF THE INVENTION

Provided herein is a nucleic acid binding nanoprobe, comprising one or more vital fluorochromes and a polymer; wherein each of the one or more vital fluorochromes is connected to the polymer; and wherein the nanoprobe comprises about 2 to about 20 vital fluorochromes per polymer.

In some embodiments, the nanoprobe is about 40 to about 1000 kDa in mass. In some embodiments, the nanoprobe is about 50 to about 400 kDa in mass. In some embodiments, the nanoprobe is about 60 to about 80 kDa in mass. In some embodiments, the nanoprobe is about 4 to about 10 nm in diameter. In some embodiments, the nanoprobe is about 4 to about 6 nm in diameter. In some embodiments, the nanoprobe comprises about 2 to about 10 vital fluorochromes per polymer. In some embodiments, the nanoprobe comprises about 3 to about 8 vital fluorochromes per polymer.

In some embodiments, the nanoprobe has structure of Formula I:

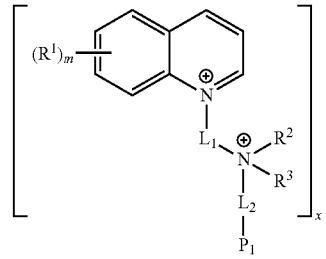

or a pharmaceutically acceptable salt thereof;
wherein:
each $L_1$ is independently $C_{2-20}$ alkylene;
each $L_2$ is independently $C_{2-20}$ alkylene, wherein any of the carbons in the $C_{2-20}$ alkylene chain is optionally replaced with C(O), O, S, S(O), S(O)$_2$, NR$^{a1}$, NR$^{b1}$C(O), or a triazole;
$P_1$ is the polymer;
each $R^1$ is independently $(CH)_t$-5-10 membered heteroaryl, $(CH)_u$-5-10 membered heterocycloalkyl, $C_{6-10}$ aryl, or NR$^{a2}$R$^{b2}$; wherein each 5-10 membered heteroaryl and 5-10 membered heterocycloalkyl has at least one ring-forming carbon atom and 1, 2, 3, or 4 ring-forming N or S atoms; and wherein the $C_{6-10}$ aryl, 5-10 membered heteroaryl, and 5-10 membered heterocycloalkyl are each optionally substituted with 1, 2, or 3 substituents independently selected from $C_{1-6}$ alkyl, NH$_2$, NH($C_{1-6}$ alkyl), and N($C_{1-6}$ alkyl)$_2$;
or two $R^1$ adjacent to each other and together with the carbon atoms to which they are attached form an $C_{6-10}$ aryl; wherein the $C_{6-10}$ aryl is optionally substituted with 1, 2, 3, or 4 substituents independently selected from $C_{1-6}$ alkyl, NH$_2$, NH($C_{1-6}$ alkyl), and N($C_{1-6}$ alkyl)$_2$;
$R^2$ and $R^3$ are independently selected from H and $C_{1-6}$ alkyl;
each R$^{a1}$, R$^{b1}$, R$^{a2}$, and R$^{b2}$ is independently selected from H and $C_{1-6}$ alkyl;
m is 1, 2, 3, 4, or 5;
t is 1, 2, 3, 4, 5, or 6;
u is 1, 2, 3, 4, 5, or 6; and
x is 2 to 20.

In some embodiments, each $L_1$ is independently $C_{3-6}$ alkylene.

In some embodiments, each $L_2$ is independently $C_{10-20}$ alkylene, wherein any of the carbons in the $C_{10-20}$ alkylene chain is optionally replaced with C(O), O, NR$^{a1}$ NR$^{b1}$C(O), or a triazole.

In some embodiments, the polymer is about 5 to about 120 kDa in mass. In some embodiments, the polymer is dextran, pullulan, dextrin, hydroxyethyl starch, amino-acid based polymer, or polyethylene glycol.

In some embodiments, each $R^1$ is independently $(CH)_t$-5-10 membered heteroaryl or $(CH)_u$-5-10 membered heterocycloalkyl. In some embodiments, each $R^1$ is (CH)-2,3-dihydrobenzo[d]thiazolyl, (CH)$_3$-benzo[d]thiazolyl, (CH)$_5$-benzo[d]thiazolyl, (CH)-2,3-dihydrobenzo[d]oxazolyl, (CH)$_5$-2,3-dihydrobenzo[d]oxazolyl, phenyl, or NH$_2$; wherein the (CH)-2,3-dihydrobenzo[d]thiazolyl, (CH)$_3$-benzo[d]thiazolyl, (CH)$_5$-benzo[d]thiazolyl, (CH)-2,3-dihydrobenzo[d]oxazolyl, (CH)$_5$-2,3-dihydrobenzo[d]oxazolyl, and phenyl each optionally substituted with 1 or 2 substituents independently selected from $C_{1-6}$ alkyl, NH$_2$;

or two R¹ adjacent to each other and together with the carbon atoms to which they are attached form a phenyl; wherein the phenyl is optionally substituted with NH₂.

In some embodiments, R¹ is (CH)-3-methyl-2,3-dihydrobenzo[d]thiazolyl.

In some embodiments, R² and R³ are $C_{1-6}$ alkyl.

In some embodiments, m is 1 or 2.

In some embodiments, t is 1, 3, or 5.

In some embodiments, u is 1, 3, or 5.

In some embodiments, x is 3, 4, 5, 6, 7, or 8.

In some embodiments:

each $L_1$ is independently $C_{3-6}$ alkylene;

each $L_2$ is independently $C_{10-20}$ alkylene, wherein any of the carbons in the $C_{10-20}$ alkylene chain is optionally replaced with C(O), O, $NR^{a1}$, $NR^{b1}C(O)$, or a triazole;

$P_1$ is a polymer;

each R¹ is independently $(CH)_t$-5-10 membered heteroaryl, $(CH)_u$-5-10 membered heterocycloalkyl, phenyl, or NH₂; wherein each 5-10 membered heteroaryl and 5-10 membered heterocycloalkyl has at least one ring-forming carbon atom and 1, 2, 3, or 4 ring-forming N or S atoms; and wherein the $C_{6-10}$ aryl, 5-10 membered heteroaryl, and 5-10 membered heterocycloalkyl are each optionally substituted with 1 or 2 substituents independently selected from $C_{1-6}$ alkyl and NH₂;

or two R¹ adjacent to each other and together with the carbon atoms to which they are attached form an $C_{6-10}$ aryl; wherein the $C_{6-10}$ aryl is optionally substituted with NH₂;

R² and R³ are independently $C_{1-6}$ alkyl;

each $R^{a1}$ and $R^{b1}$ is independently selected from H and $C_{1-6}$ alkyl;

m is 1, 2, 3, 4, or 5;

t is 1, 2, 3, 4, 5, or 6;

u is 1, 2, 3, 4, 5, or 6; and x is 3 to 8.

In some embodiments, the moiety

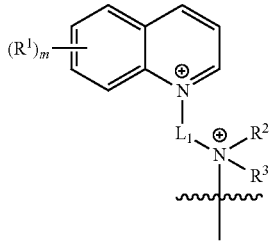

is selected from:

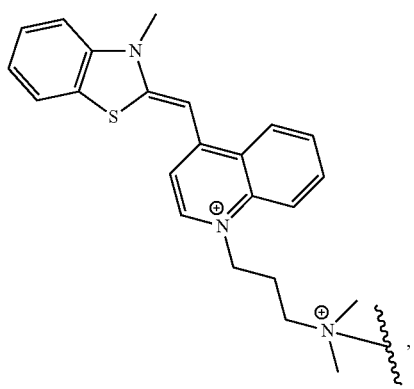

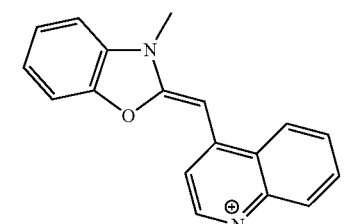

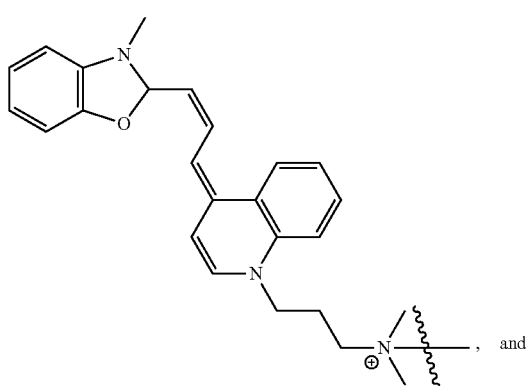

-continued

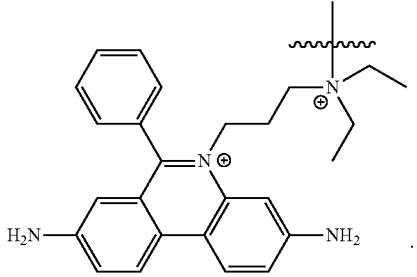

In some embodiments, the nanoprobe is

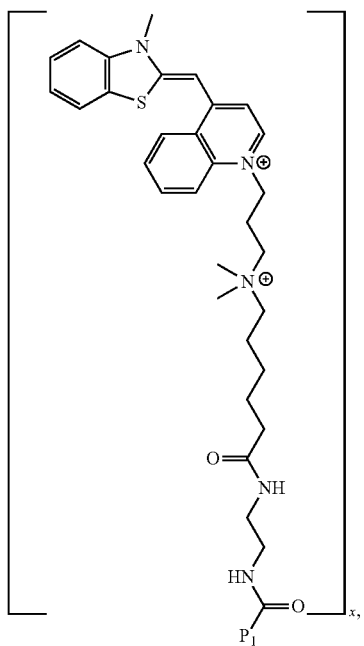

or a pharmaceutically acceptable salt thereof; wherein x is 2 or 3; $P_1$ is dextran, wherein the dextran is about 40 kDa in mass.

In some embodiments, the vital fluorochrome is

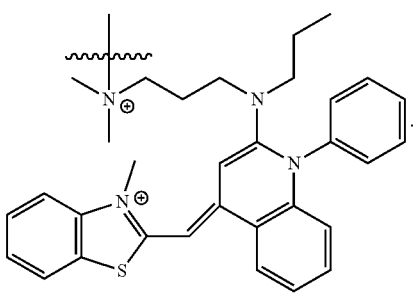 [SMILES: *[N+](C)(C)CCCN(CCC)C1=C/C(=C\c2sc3ccccc3[n+]2C)c2ccccc2N1c1ccccc1]

This disclosure further provides a pharmaceutical composition comprising one or more nanoprobes as described herein and one or more pharmaceutically acceptable excipients. In some embodiments, the excipient is a buffer agent or a saline solution.

This disclosure also provides a method of treating or preventing damage (e.g., cellular damage) from an injury or an infection in a subject comprising administering to the subject a therapeutically effective amount of a nanoprobe or a composition as described herein.

Further, this disclosure provides a method of suppressing an immune response resulting from an injury or an infection in a subject comprising administering to the subject a therapeutically effective amount of a nanoprobe or a composition as described herein.

Furthermore, this disclosure provides a method of imaging one or more sites of an injury or an infection in a subject, the method comprising:

administering to the subject a nanoprobe of or a composition as described herein; and obtaining an image of the nanoprobe in the subject.

In some embodiments, the injury or infection is selected from the group consisting of ischemic injury (e.g., ischemia-reperfusion, infarction, shock, and cardiac arrest); tissue injury secondary to rheumatological and autoimmune diseases; tissue injury due to burns, toxins and hyperthermia; mechanical injury (e.g., military injuries, car accidents, gunshots, and blasts); infection (e.g., bacterial, viral and fungal); sepsis; and transplant rejection. In some embodiments, the subject is a human or an animal.

Other features and advantages of the invention will be apparent from the following detailed description and figures, and from the claims.

BRIEF DESCRIPTION OF THE DRAWINGS

FIG. 1A shows a 40 kDa amino dextran is reacted with the TO-NHS (N-hydroxysuccinimide) to yield the Dex-TO nanoprobe with an average of 2.8 TO per particle (dextran).

FIG. 1B shows the control material, Dex-Cy5.5, has an average of 3 Cy5.5 per particle (dextran).

FIG. 1C and FIG. 1D are flow cytometry scattergrams of Dex-TO and the reference intravital fluorochrome Sytox-blue. The scattergrams show that the Dex-TO nanoprobe is excluded from healthy cells, and taken up by sytox positive, necrotic cells.

FIG. 1E is confocal microscopy showing that Dex-TO uptake is nuclear and colocalizes with Sytox Blue.

FIG. 1F is a graph showing that Dex-TO fluorescence increases steeply with DNA concentration (top line), while substantially less increase is seen with TO-PRO 1 (second from the top) and none with Dex-Cy5.5 (bottom line) or Cy5.5 (bottom line).

FIG. 1G and FIG. 1H are graphs that show Dex-TO, as determined by FPLC against known standards, has a molecular weight of 51 kDa and a diameter of 4.9 nm.

FIG. 1I is a graph that shows in the presence of DNA, Dex-TO forms multimeric clusters, which reach a size of 200-300 nm by light scattering. FPLC standards: conalbumin (C), ovalbumin (O), carbonic anhydrase (CA), RNase A (R), aprotinin (Apr).

FIG. 2A is a graph showing that the lifetime fluorescence of Dex-TO increases in the presence of DNA (top line). Dex-TO only is represented by the middle line and the background is represented by the bottom line.

FIG. 2B are images that show that the lifetime of Dex-TO increases in the anterior wall of an infarcted left ventricle, but not in the uninjured septum.

FIG. 2C is the TTC staining of the same heart slice as in FIG. 2B.

FIG. 2D is a continuous wave fluorescence imaging of an infarcted mouse heart after Dex-TO and Dex-Cy5.5 co-injection, followed by TTC staining. Dex-TO uptake is confined to the TTC-negative pale area.

FIG. 3G from left to right: first and second bars represent $^{111}$In-TO, third and fourth bars represent Dex-TO, fifth and sixth bars represent Dex-Cy5.5, and seventh and eight bars represent Gd-TO. $p<0.01$, *$p<0.001$, ****$p<0.0001$, ns=not significant.

FIG. 5A to FIG. 5D are graphs showing Dex-TO fluorescence increases in the presence of proinflammatory nucleic acid species.

FIG. 6A is a diagram of the protocol of the Dex-TO dosing regimen and the endpoints at 24 hrs (CD68 immunohistochemistry), and at 7 days (TTC staining).

FIG. 6B and FIG. 6C are images of the control mice. A dense infiltrate of CD68 positive cells was seen at 24 hours throughout the area-at-risk (AAR), delineated in FIG. 6C by the absence of microspheres (denoted by outline).

FIG. 6D and FIG. 6E are images showing that the infiltration of CD68 positive cells into the AAR at 24 hours was markedly reduced by Dex-TO injection.

DETAILED DESCRIPTION

Figure 2F:
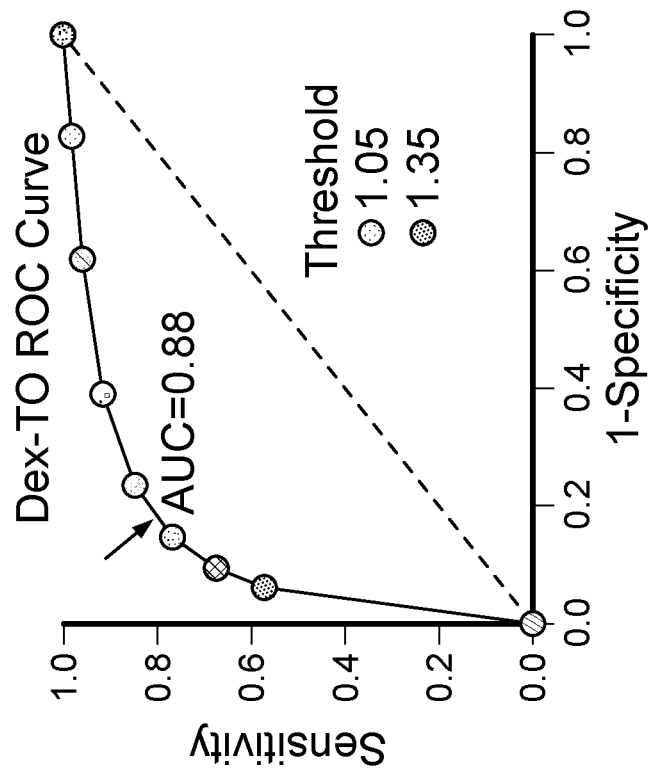
FIG. 2F is a graph showing that Dex-TO detects necrosis with high sensitivity and specificity (AUC=0.88), with an optimal threshold (arrow) of 27% above the septal signal.

This disclosure describes nucleic acid (NA) binding nanoprobes, their binding to NAs, their use in limiting damage from injury or infection in animals or humans, and their use as imaging agents in the sites of injuries. Injuries include various forms of ischemic injury, mechanical injury, burns, hyperthermia, autoimmune disease, and toxins. The NA-binding nanoprobes provide a design for a new class of immune suppressive pharmaceuticals. The nanoprobes include one or more vital fluorochromes and a polymer, where each of the vital fluorochromes is connected to the polymer by a linker. The vital fluorochrome of the nanoprobe can bind to released NAs, which allows the location and extent of the injury to be visualized by imaging the nanoprobe using various imaging methods. Once the nanoprobe binds to NAs it attenuates their ability to stimulate cyctokine release from monocytes and macrophages. The inhibition of cytokine release by the nanoprobes can reduce the infiltration of additional immune cells into the site of injury and thus prevent an excessive immune response. By attenuating the immune response to injury, and preventing an excessive response of the immune response, the nanoprobes can reduce tissue damage.

Further, the nanoprobes can be detected in the subject by various imaging modalities including, e.g., single photon emission computed tomography (SPECT), positron emission tomography (PET), magnetic resonance imaging (MRI) or other imaging modality. Thus, the nanoprobes described herein can be useful as imaging agents to detect the location and extent of the injury.

Provided herein is a nucleic acid binding nanoprobe, comprising one or more vital fluorochromes and a polymer; wherein each of the one or more vital fluorochromes is connected to the polymer; and wherein the nanoprobe comprises about 2 to about 20 vital fluorochromes per polymer. The size of the polymer can be optimized for circulation half-life and tissue penetration.

The nanoprobe can be about 40 to about 1000 kDa in mass. In some examples, the nanoprobe is about 50 to about 300, about 50 to about 200, about 50 to about 100, or about 60 to about 100 kDa in mass. The nanoprobe can be about 50 to about 400 or about 60 to about 80 kDa in mass.

The nanoprobe can be about 4 to about 10, about 4 to about 8, or about 4 to about 6 nm in diameter. In some examples, the nanoprobe is about 4, about 5, about 6, about 7, about 8, about 9, or about 10 nm in diameter.

The nanoprobe can include about 2 to about 10 vital fluorochromes per polymer. In some examples, the nanoprobe includes about vital 3 to about 8 fluorochromes per polymer. In some examples, the nanoprobe includes about 2, about 3, about 4, about 5, about 6, about 7, about 8, about 9, or about 10 vital fluorochromes per polymer.

In some embodiments, the nanoprobe can be presented by the structure of Formula I:

![Structure I showing quinolinium with (R¹)ₘ substituents, L₁ linker to N⁺ bearing R², R³, L₂, and P₁, in brackets subscript x]

I or a pharmaceutically acceptable salt thereof;
wherein:
each $L_1$ is independently $C_{2-20}$ alkylene;
each $L_2$ is independently $C_{2-20}$ alkylene, wherein any of the carbons in the $C_{2-20}$ alkylene chain is optionally replaced with C(O), O, S, S(O), S(O)$_2$, NR$^{a1}$, NR$^{b1}$C(O), or a triazole;
$P_1$ is the polymer;
each $R^1$ is independently (CH)$_t$-5-10 membered heteroaryl, (CH)$_u$-5-10 membered heterocycloalkyl, $C_{6-10}$ aryl, or NR$^{a2}$R$^{b2}$; wherein each 5-10 membered heteroaryl and 5-10 membered heterocycloalkyl has at least one ring-forming carbon atom and 1, 2, 3, or 4 ring-forming N or S atoms; and wherein the $C_{6-10}$ aryl, 5-10 membered heteroaryl, and 5-10 membered heterocycloalkyl are each optionally substituted with 1, 2, or 3 substituents independently selected from $C_{1-6}$ alkyl, NH$_2$, NH(C$_{1-6}$ alkyl), and N(C$_{1-6}$ alkyl)$_2$;
or two $R^1$ adjacent to each other and together with the carbon atoms to which they are attached form an $C_{6-10}$ aryl; wherein the $C_{6-10}$ aryl is optionally substituted with 1, 2, 3, or 4 substituents independently selected from $C_{1-6}$ alkyl, NH$_2$, NH(C$_{1-6}$ alkyl), and N(C$_{1-6}$ alkyl)$_2$;
$R^2$ and $R^3$ are independently selected from H and $C_{1-6}$ alkyl;
each R$^{a1}$, R$^{b1}$, R$^{a2}$, and R$^{b2}$ is independently selected from H and $C_{1-6}$ alkyl;
m is 1, 2, 3, 4, or 5;
t is 1, 2, 3, 4, 5, or 6;
u is 1, 2, 3, 4, 5, or 6; and
x is 2 to 20.
In some examples, each $L_1$ is independently $C_{3-6}$ alkylene.
In some examples, each $R^1$ is independently (CH)$_t$-5-10 membered heteroaryl or (CH)$_u$-5-10-membered heterocycloalkyl.
In some examples, each $R^1$ is (CH)-2,3-dihydrobenzo[d]thiazolyl, (CH)$_3$-benzo[d]thiazolyl, (CH)$_5$-benzo[d]thiazolyl, (CH)-2,3-dihydrobenzo[d]oxazolyl, (CH)$_5$-2,3-dihydrobenzo[d]oxazolyl, phenyl, or NH$_2$; wherein the (CH)-2,3-dihydrobenzo[d]thiazolyl, (CH)$_3$-benzo[d]thiazolyl, (CH)$_5$-benzo[d]thiazolyl, (CH)-2,3-dihydrobenzo[d]oxazolyl, (CH)$_5$-2,3-dihydrobenzo[d]oxazolyl, and phenyl each optionally substituted with 1 or 2 substituents independently selected from $C_{1-6}$ alkyl, NH$_2$;
or two $R^1$ adjacent to each other and together with the carbon atoms to which they are attached form a phenyl; wherein the phenyl is optionally substituted with NH$_2$.
In some examples, $R^1$ is (CH)-3-methyl-2,3-dihydrobenzo[d]thiazolyl.
In some examples, $R^2$ and $R^3$ are $C_{1-6}$ alkyl.
In some examples, m is 1 or 2. In some examples, t is 1, 3, or 5. In some examples, u is 1, 3, or 5. In some examples, x is 3, 4, 5, 6, 7, or 8.

In some embodiments:
each $L_1$ is independently $C_{3-6}$ alkylene;
each $L_2$ is independently $C_{10-20}$ alkylene, wherein any of the carbons in the $C_{10-20}$ alkylene chain is optionally replaced with C(O), O, NR$^{a1}$, NR$^{b1}$C(O), or a triazole;
$P_1$ is a polymer;
each $R^1$ is independently (CH)$_t$-5-10 membered heteroaryl, (CH)$_u$-5-10 membered heterocycloalkyl, phenyl, or NH$_2$; wherein each 5-10 membered heteroaryl and 5-10 membered heterocycloalkyl has at least one ring-forming carbon atom and 1, 2, 3, or 4 ring-forming N or S atoms; and wherein the $C_{6-10}$ aryl, 5-10 membered heteroaryl, and 5-10 membered heterocycloalkyl are each optionally substituted with 1 or 2 substituents independently selected from $C_{1-6}$ alkyl and NH$_2$;
or two $R^1$ adjacent to each other and together with the carbon atoms to which they are attached form an $C_{6-10}$ aryl; wherein the $C_{6-10}$ aryl is optionally substituted with NH$_2$;
$R^2$ and $R^3$ are independently $C_{1-6}$ alkyl;
each R$^a$ and R$^{b1}$ is independently selected from H and $C_{1-6}$ alkyl;
m is 1, 2, 3, 4, or 5;
t is 1, 2, 3, 4, 5, or 6;
u is 1, 2, 3, 4, 5, or 6; and
x is 3 to 8.
In some embodiments, the nanoprobe can be represented by the following structure:

![Specific nanoprobe structure with benzothiazole, quinolinium, alkyl chain, amide linkages connected to P₁, in brackets subscript x]

or a pharmaceutically acceptable salt thereof; wherein x is 2 or 3; $P_1$ is dextran, wherein the dextran is about 40 kDa in mass.

The nanoprobes described herein differ from monovalent NA binding fluorochromes where a single NA binding fluorochrome per mole is employed, which typically have molecular weights smaller than 2000 Da. See e.g., WO2010/141833, the content of which is incorporated herein by reference. These monovalent fluorochromes are detectable by fluorescence and an additional modality by virtue of attached metals like Gd$^{3+}$ (MRI) or $^{111}$In(SPECT). Generally, these compounds are not as effective as immune suppressive agents because they have lower affinity for NA (monovalent), and their small size can lead to rapid renal elimination and excessively short circulation half-lives, which limits their usefulness as immune suppressive agents.

The nanoprobes described herein also differ from nanoparticle based NA binding fluorochromes in the literature where more than one NA binding fluorochrome per mole is attached to a large magnetic nanoparticle, such as ferumoxytol (FH) (Cho, H., et al., (2013), ACS nano 7, 2032-41; Cho, H., et al., (2013) Inorganic chemistry 52, 12216-22). Fluorochrome-bearing magnetic nanoparticles have been used to image NAs with MRI, but their large size (which is approximately one million kDa, or a diameter >20 nm) leads to poor tissue penetration and rapid clearance by phagocytosis in the liver and spleen. This can limit their usefulness as immune suppressive agents.

For example, thiazole-orange (TO) is a fluorochrome and can be conjugated to gadolinium chelates and large nanoparticles, such as Feraheme (FH), to create diagnostic imaging agents (Cho H, et al., ACS Nano. 2013; 7: 2032-41; Garanger E, et al., Chem Commun (Camb). 2009: 4444-6; Huang S, et al., Circ Cardiovasc Imaging. 2011; 4: 729-37). These biomaterials can have limitations both as diagnostic and therapeutic agents. For example, Gadolinium-TO is monovalent and can have a relatively low affinity for NAs and be rapidly cleared by glomerular filtration. On the other hand, the far larger FH-TO nanoparticle exhibits poor tissue penetration and rapid clearance by the cells of the reticuloendothelial system (Montet-Abou K, et al., Eur Heart J. 2010; 31: 1410-20). In addition, the repeated use of FH-TO is limited by iron's slow excretion and toxicity.

Dextran-TO (Dex-TO) as described in the Examples is an iron-free multivalent NA-binding nanoprobe that can detect, image and scavenge released NAs at sites of injury.

Various features of the nanoprobes described herein can be tuned, e.g., varying polymer size and type (e.g., pharmacokinetics), varying valency (e.g., number of NA-binding fluorochromes per polymer), and varying the chemistry of the NA-binding fluorochrome.

As used herein, "alkyl" refers to a hydrocarbon chain that may be a straight chain or branched chain, containing the indicated number of carbon atoms. For example, $C_{1-12}$ alkyl indicates that the group may have from 1 to 12 (inclusive) carbon atoms.

As used herein, "alkylene" refers to refers to a divalent hydrocarbon chain that may be a straight chain or branched chain, containing the indicated number of carbon atoms. An alkylene group is generally a linking alkane group with two C—H bond replaced by points of attachment to the remainder of the compound.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms.

As used herein, "heteroaryl" groups refer to aromatic heterocycles having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, and indolinyl. In some embodiments, the heteroaryl group has from 1 to about 20 carbon atoms. In some embodiments, the heteroaryl group contains 3 to about 14 ring-forming atoms. In other embodiments, the heteroaryl group has 1 to about 4 heteroatoms.

As used herein, the term "heterocycloalkyl" refers to non-aromatic heterocycles having at least one heteroatom ring member such as sulfur, oxygen, or nitrogen. Heterocycloalkyl can include 4-10 ring members, 4-7 ring members, or 4-6 ring members. Heterocycloalkyl groups can include mono- or bicyclic or spirocyclic ring systems. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. Heterocycloalkyl also include groups that have one or more aromatic rings fused to the heterocycloalkyl ring, e.g., benzo or thienyl derivatives of piperidine, morpholine, azepine, etc.

The term "pharmaceutically acceptable salts" refers to when the compounds provided herein is converted to their salt forms. Examples of pharmaceutically acceptable salts include inorganic or organic acid salts. The pharmaceutically acceptable salts can be synthesized from basic or acidic moiety of the compound provided herein by conventional chemical methods. The nanoprobe provided herein can be positively charged and anions can be associated with the charged nanoprobe to form a salt. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002).

Vital Fluorochromes

Vital fluorochromes (VF) are generally low molecular weight organic compounds, e.g., less than about 800 Daltons, and contain two parts: 1) a monocyclic or polycyclic ring and 2) an alkylene linker connected to a terminal quaternary nitrogen. Vital fluorochromes are generally positively charged. The linker has two ends, and its first end is attached to the ring system and its second end is attached to a terminal quaternary nitrogen that is generally positively charged. The positive charge assists in preventing the VFs from passing through intact membranes and binding to nucleic acids in healthy cells. The ring system is typically unsaturated, which can give rise to absorption and emission (Abs/em) of light (fluorescence). The rings intercalate between the bases of double-stranded DNA and thus, is able to bind to nucleic acid with high affinity. VFs can also show weaker binding to single-stranded nucleic acids. In addition to playing a role in making the VF membrane impermeable, positive charges on the VF can also assist in tight DNA binding, by interacting with negatively charged phosphate groups on the DNA backbone.

In some embodiments, the vital fluorochromes can be represented by the following moiety:

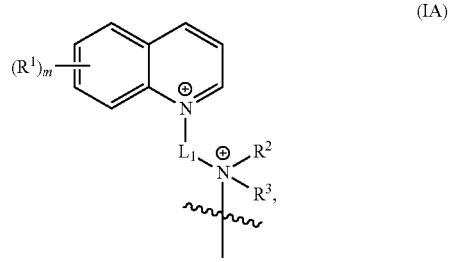

(IA)

where $R^1$, $R^2$, $R^3$, m and $L_1$ are as described herein. The wavy bond denotes the point of attachment to a linker (e.g., $L_2$ as described herein), which is connected to a polymer. The vital fluorochrome is typically positively charged at the quinoline nitrogen, or the positive charge can be delocalized into the $R^1$ group. The vital fluorochrome can also include a positive charge on the nitrogen of the $NR^2R^3$ group. In some examples, the vital fluorochrome has two positive charges.

The moiety

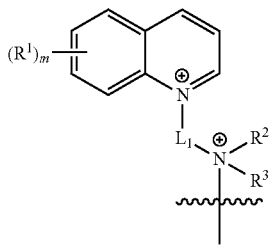

can be

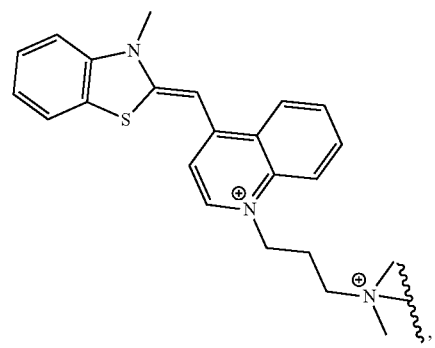

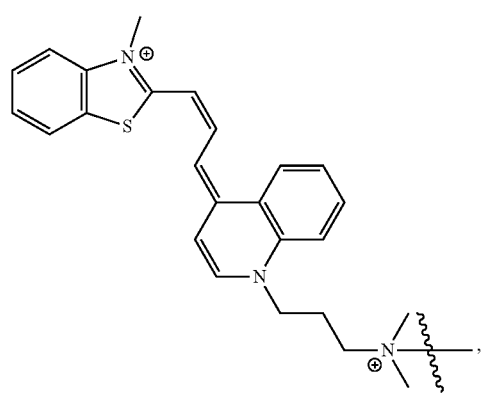

-continued

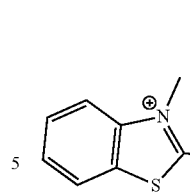

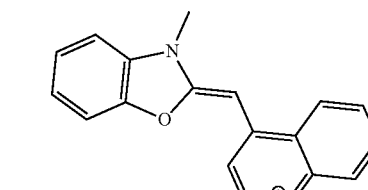

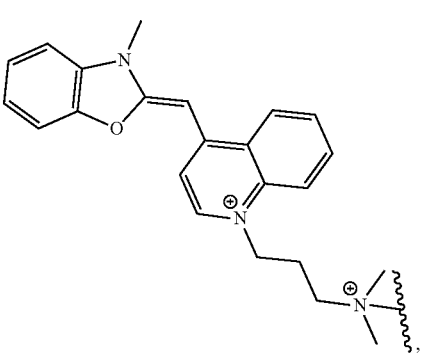

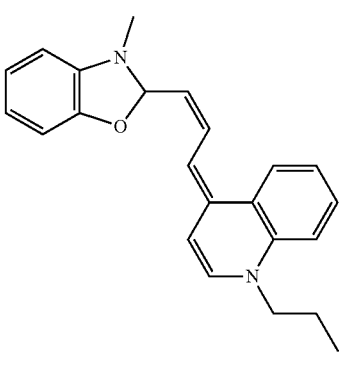, or

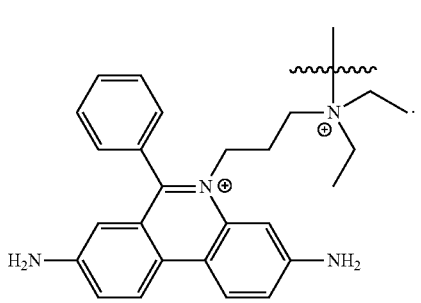

In some examples, the vital fluorochrome is

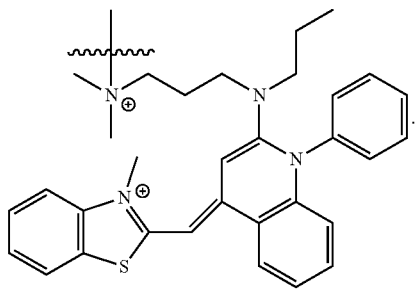 [SMILES: *[N+](C)(C)CCCN(CCC)C1=C/C(=C\c2sc3ccccc3[n+]2C)c2ccccc2N1c1ccccc1]

Exemplary VFs include thiazole-orange (TO), which is a vital fluorochrome that binds to NAs but not to serum proteins. Examples of VFs and their optical properties are described in the table below.

| VFs and their Optical Properties | | |
|---|---|---|
| VF | VF Structure | Abs/em |
| TO-PRO 1 | | 515/531 (nm) |
| TO-PRO 3 | | 612/631 |
| TO-PRO 5 | | 745/770 |
| YO-PRO | | 491/509 |
| YO-PRO 3 | | 612/631 |
| Propidium Iodide (PI) | | 530/625 |
| Sybr Green | | 490/520 |

Linkers

The term "linker" as used herein refers to $L_2$ moiety in Formula I, where $L_2$ is a $C_{2-20}$ alkylene group, where any of the carbons in the $C_{2-20}$ alkylene chain is optionally replaced with C(O), O, S, S(O), S(O)$_2$, NR$^{a1}$ NR$^{b1}$C(O), or a triazole. In some examples, each $L_2$ is independently $C_{10-20}$ alkylene, wherein any of the carbons in the $C_{10-20}$ alkylene chain is optionally replaced with C(O), O, NR$^{a1}$, NR$^{b1}$C(O), or a triazole. The linker is connected at a first end to the vital fluorochrome through the quaternary nitrogen on the aliphatic arm. Thus, in order for the linker to be installed onto the VF and yield a quaternary nitrogen, the linker must have an amino group on the first end (see intermediate 2 in Scheme 1) which can displace the halide intermediate (see intermediate 1 in Scheme 1) and produce the quaternary nitrogen. In addition, the linker is connected at a second end to $P_1$ (a polymer) through a covalent bond. Alternatively, a first linker can be extended with a second linker, to produce a longer and more complex linker, prior to attachment of polymer group. Exemplary linkers are shown in the table below.

| Linker |
|---|
| (structure) |
| (structure) |
| (structure) |

Polymer

The nanoprobes described herein include a polymer that is connected to one or more fluorochromes through a linker. The polymer can be about 5 to about 120 kDa in mass. In some examples, the polymer can be about 10 to about 100, about 10 to about 80, about 20 to about 80, about 20 to about 60, or about 30 to about 50 kDa in mass. For example, the polymer can be 40 kDa in mass. Examples of the polymer include dextran, pullulan, dextrin, hydroxyethyl starch, amino-acid based polymer, or polyethylene glycol. For example, the polymer can be a polysaccharide such as a dextran (e.g., a 40 kDa dextran).

Nanoprobe Synthesis

A series of nanoprobes can be prepared by the methods outlined below in Scheme 1. Unsaturated ring intermediate 1 wherein X is a halide such as iodide or bromide is subjected to a nucleophilic attack reaction with the tertiary amine 2 wherein L is the linker to give the quaternary amine 3. Other good leaving groups which can be employed in this reaction include sulfonate esters such as mesylate or tosylate groups. This step directly attaches the linker to the vital fluorochrome through the quaternary amine. The linker must carry a reactive group (Y) that can be used to attach the reporter group to the vital fluorochrome and linker intermediate 3. Reactive groups (Y) that are useful include an amine or carboxyl acid or ester which can undergo an amide coupling reaction. Alternatively, a reactive group such as an azide or terminal alkyne can also be used for attachment of the reporter group using "click" chemistry. The polymer ($P_1$—Z) is then attached to the linker through the reactive group (Z). If amide coupling chemistry is used to attach the reporter group to the linker then Y can be either an amino group or a carboxylic acid or ester. If "click" chemistry is employed to install the reporter group onto the linker then Y can be either an azide or terminal alkyne and Z can be either an azide or terminal alkyne.

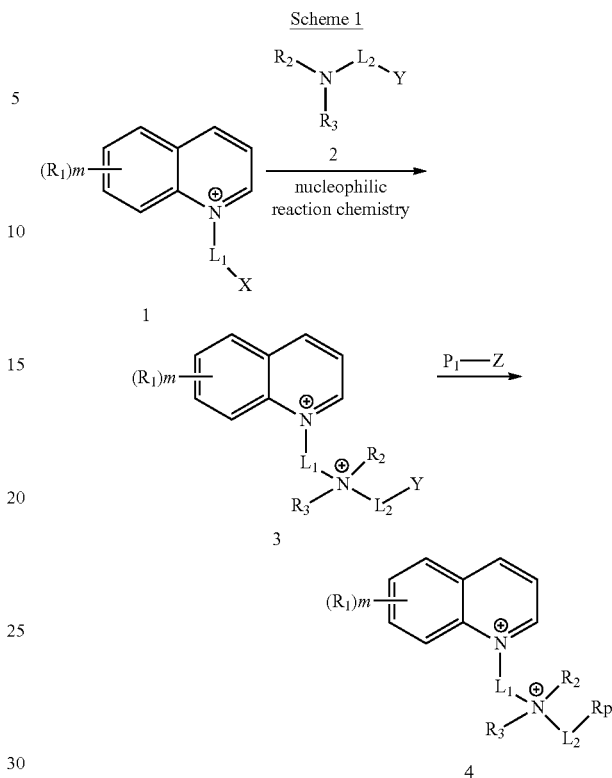

Scheme 1

Alternatively, the linker can be initially attached to a $P_1$ polymer group to form amine 6, which then undergoes a reaction with 5 to produce the conjugate 7 as shown in Scheme 2. X in 5 can be an NHS ester; and each Lx in 5 and 6 can be a linker such that when 5 and 6 are coupled together, the Lx's combine to form $L_2$.

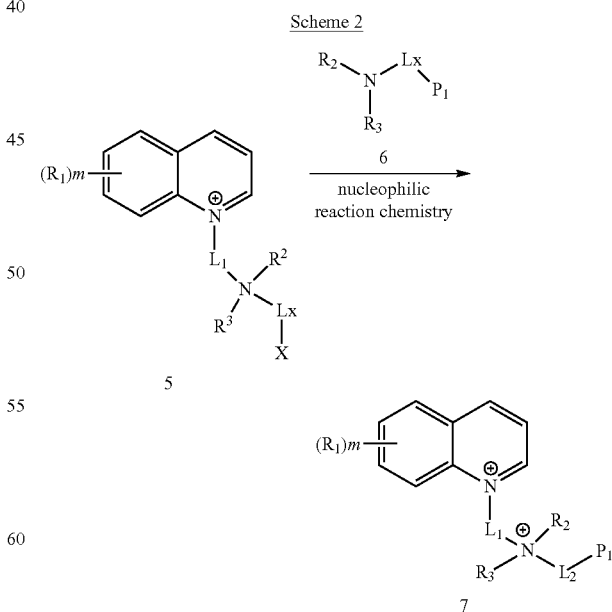

Scheme 2

Methods of Detecting and Using Nanoprobes

Cell rupture and the exposure of NAs to the immune system can result from a variety of insults including ischemia, mechanical trauma, toxins, burns, sepsis, transplant rejection and autoimmune disease. Released NAs are highly pro-inflammatory and result in further tissue damage due to their excessive stimulation of the immune response. Provided herein are methods of treating or preventing damage (e.g., cellular damage) from an injury or an infection in a subject comprising administering to the subject a therapeutically effective amount of a nanoprobe or a composition described herein. The present disclosure also includes methods of reducing damage from an injury or an infection in a subject comprising administering to the subject a therapeutically effective amount of a nanoprobe or a composition described herein.

The subject includes human and animal subjects. In some embodiments, provided herein are methods of suppressing an immune response resulting from an injury or an infection in a subject comprising administering to the subject a therapeutically effective amount of a nanoprobe or a composition described herein.

In some embodiments, provided herein are method of imaging one or more sites of an injury or an infection in a subject, the method comprising:

administering to the subject a nanoprobe or a composition of described herein; and obtaining an image of the nanoprobe in the subject.

The nanoprobes described herein are multivalent NA-binding nanoprobes that can detect tissue injury, and further can exert anti-inflammatory and cytoprotective effects at the site of injury. The theranostic (diagnostic and therapeutic) capabilities of the nanoprobes provide a new paradigm for the rapid diagnosis and simultaneous treatment of tissue injury. Examples of injury include ischemia-reperfusion, infarction, cardiac arrest and shock. Tissue injury can also result from mechanical trauma (e.g., military injuries, car accidents, gunshot wounds, and blasts), burns, toxins, hyperthermia and autoimmune disease.

The fluorescent nature of the probe can allow its disposition in cells and mechanism of action to be determined. The intercalation of the nanoprobe with NAs can provide a stable and specific signature of NA binding as well as a mechanism of signal amplification. Free NAs can form large nanoclusters upon binding to nanoprobe, which can markedly reduce their ability to stimulate cytokine release from activated leukocytes. This can attenuate further macrophage infiltration into the site of injury and ultimately reduce the extent of injury. For example, an 18% reduction in day-seven myocardial infarct size was produced by the nanoprobe Dex-TO (dextran-thiazole orange conjugate; see examples for details), which compares extremely favorably with the reduction in infarct size produced by other anti-inflammatory approaches, such as siRNA to the chemokine receptor CCR2 (Leuschner F, et al., Nat Biotechnol. 2011; 29: 1005-10).

The therapeutic effect of the nanoprobe is thought to be attributed to its specific intercalation with NAs, which is an improvement over DNA scavenging polymers that rely on electrostatic forces (Jain S, et al., Proc Natl Acad Sci USA. 2012; 109: 12938-43; Stearns N A, et al., PloS one. 2012; 7: e40862). The positive charge of these DNA scavenging polymers can potentially attenuate NA immunogenicity but can also result in non-specific binding to the many sources of negative charge in vivo, including peptidoglycans (e.g. heparin), negatively charged lipids, cell membranes and proteins (albumin). Nevertheless, recent studies have shown that DNA scavenging materials relying on electrostatic forces can be used to treat thrombosis (Jain S, et al., Proc Natl Acad Sci USA. 2012; 109: 12938-43), block DNA binding to anti-DNA antibodies in systemic lupus erythematosus (Stearns N A, et al., PloS one. 2012; 7: e40862), and modulate the innate immune response (Holl E K, et al., PloS one. 2013; 8: e69413). However, none of the electrostatic scavengers reported to date have the theranostic capability of the nanoprobe described herein, and the ability to combine a diagnostic imaging readout with efficient NA scavenging.

The attenuation of NA-induced tissue injury has also been attempted with DNase, RNase, small chemicals, and TLR inhibitors (Cavassani K A, et al., J Exp Med. 2008; 205: 2609-21; Chen C, et al., J Am Heart Assoc. 2014; 3: e000683; Vogel B, et al., Basic Res Cardiol. 2015; 110: 15; Fuchs T A, et al., Proc Natl Acad Sci USA. 2010; 107: 15880-5; Barrat F J, et al., Eur J Immunol. 2007; 37: 3582-6; Plitas G, et al., J Exp Med. 2008; 205: 1277-83; Cabrera-Fuentes H A, et al., Thromb Haemost. 2014; 112: 1110-9; Shak S, et al., Proc Natl Acad Sci USA. 1990; 87: 9188-92). These agents, however, have short serum half-lives, need to be administered frequently and at a high dose, and are costly. RNase injected intravenously may also not be effectively delivered into the interstitial space where the extracellular NAs are released.

The nanoprobes described herein, in addition to its theranostic nature, have several advantages over these approaches. The nanoprobes described herein can scavenge both DNA and RNA and act upstream of pathways in the innate immune response that are stimulated by NAs. The efficiency of the nanoprobe binding to NA is high, with an $EC_{50}$ as low as 0.06 nM for bacterial DNA. In addition, the nanoprobe is devoid of trace metals and high therapeutic doses could potentially be used without the risk of toxicity.

For example, the nanoprobe Dex-TO consists of a 40 kDa dextran carrier to which three TO molecules are attached. A 40 kDa carrier was selected based on studies of dextran pharmacokinetics in mice, which indicate that this dextran undergoes rapid extravasation along with moderately slow excretion (Dreher M R, et al., J Natl Cancer Inst. 2006; 98: 335-44; Takakura Y, et al., Pharm Res. 1996; 13: 820-31). Without being limited to a particular nanoprobe, other polymeric carriers and NA binding fluorochromes can be used to provide nanoprobes that are useful as NA binding theranostics, each optimized for specific conditions.

Theranostic fluorescent nanoprobes, such as Dex-TO, can be used in organs that can be imaged with surface fluorescence imaging or endoscopy. This includes the retina, skin, lungs, urogenital and gastrointestinal tracts. Fluorescence imaging is being increasingly used in open surgical procedures and the nanoprobes described herein can be useful in these procedures. A nanoprobe described herein, e.g., Dex-TO, can be useful for early diagnosis and treatment of traumatic injury by early responders in the field. In addition, the nanoprobes' affinity for bacterial DNA can make it particularly effective in the treatment of sepsis.

The nanoprobes described herein can be imaged by MR imaging (MRI), positron emission tomography (PET), single photon computerized tomography (SPECT), or other whole body imaging modalities either alone or in combination with other traditional imaging modalities such as NIR imaging. The vital fluorochrome of nanoprobes can be imaged by these whole body imaging modalities to detect sites of injuries. Additionally, these vital fluorochromes can be detected by traditional fluorescence imaging techniques allowing for the facile tracking of the vital fluorochrome by fluorescence microscopy or flow cytometry using methods known in the art, e.g., as described in US 2005/0249668.

The nanoprobes and compositions described herein can be used in in vivo imaging methods to identify and evaluate cell injuries. In general, such methods include administering to a subject one or more nanoprobes described herein; optionally allowing the nanoprobe to distribute within the subject; exposing the subject to light of a wavelength absorbable by the vital fluorophore (VF) to determine the position of the VF; and imaging the subject by either MRI, PET, SPECT, or other whole body imaging modality to detect the presence of injuries in the subject. Furthermore, it is understood that the methods (or portions thereof) can be repeated at intervals to evaluate the subject over time.

Information provided by such in vivo imaging, for example, the presence, absence, or level of emitted signal, can be used to detect and/or monitor tissue damage, inflammation, and/or disease in the subject. Examples of causes of tissue damage include, without limitation, ischemic injury (e.g., ischemia-reperfusion, infarction, shock and cardiac arrest); tissue injury secondary to rheumatological and autoimmune diseases; tissue injury due to burns, toxins and hyperthermia; mechanical injury (e.g., military injuries, car accidents, gunshots, and blasts); infection (e.g., bacterial, viral and fungal); sepsis; and transplant rejection. Other examples of tissue damage include Alzheimer's disease, atherosclerosis, cancer, stroke, inflammatory bowel disease, diabetes, and organ transplant.

In addition, in vivo imaging can be used to assess the effect of the nanoprobe has on reducing damage due to injuries, or as an imaging agent to assess the effect of a compound or therapy, by using the nanoprobe described herein. The subject can be imaged prior to and after treatment with the compound or therapy, and the corresponding signal/images are compared. The methods and compositions disclosed herein can also be used to monitor and/or guide various therapeutic interventions, such as surgical procedures, and monitoring drug therapy, including cell based therapies.

With respect to in vitro imaging methods, the compounds and compositions described herein can be used in a variety of in vitro assays. An exemplary in vitro imaging method comprises: contacting a sample, for example, a biological sample, with one or more nanoprobes described herein; allowing the nanoprobe to interact with a biological target in the sample; optionally, removing unbound nanoprobe; illuminating the sample with light of a wavelength absorbable by a fluorophore of the agents; and detecting a signal emitted from fluorophore thereby to determine whether the agent has been activated by or bound to the biological target.

After a nanoprobe is synthesized and optionally formulated, it can be tested in vitro by one skilled in the art to assess its biological and performance characteristics. For instance, different types of cells grown in culture can be used to assess the biological and performance characteristics of the nanoprobe. Cellular uptake, binding or cellular localization of the nanoprobe can be assessed using techniques known in the art, including, for example, fluorescent microscopy, fluorescence-activated cell sorting (FACS) analysis, immunohistochemistry, immunoprecipitation, in situ hybridization and Forster resonance energy transfer (FRET) or fluorescence resonance energy transfer. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the nanoprobes. Other detection methods including, but not limited to flow cytometry, immunoassays, hybridization assays, and microarray analysis can also be used.

The terms "treat," "treating," or "treatment," refer to reversing, inhibiting, or alleviating the disease, condition, or disorder in a subject who is experiencing or displaying the pathology or symptomatology of the disease, condition or disorder.

The terms "prevent," "preventing," or "prevention," refer to reducing the risk of having a disease, condition, or disorder in a subject who may be predisposed to the disease, condition or disorder but does not yet experience or display the pathology or symptomatology of the disease, condition or disorder.

Compositions

Provided herein are pharmaceutical compositions comprising one or more nanoprobes described herein and one or more pharmaceutically acceptable excipients. The nanoprobes described herein can be provided dry or dissolved in a carrier or vehicle, e.g., pharmaceutically acceptable carriers and vehicles. Useful carriers and vehicles include, but are not limited to, buffer agent/substances such as phosphate, glycine, sorbic acid, potassium sorbate, tris(hydroxymethyl)amino methane ("TRIS"), partial glyceride mixtures of fatty acids, water, salts or electrolytes, disodium hydrogen phosphate, potassium hydrogen phosphate, and sodium chloride. The excipient can be a buffer agent or a saline solution.

The nanoprobe can be administered in the form of a sterile injectable preparation. The possible vehicles or solvents that can be used to make injectable preparations include water, Ringer's solution, and isotonic sodium chloride solution, and 5% D-glucose solution (D5W). In addition, oils such as mono- or di-glycerides and fatty acids such as oleic acid and its derivatives can be used. The compounds and compositions can be administered orally, parenterally, by inhalation, topically, rectally, nasally, buccally, vaginally, or via an implanted reservoir. The term "parenteral administration" includes intravenous, intramuscular, intra-articular, intrasynovial, intrasternal, intrathecal, intraperitoneal, intracisternal, intrahepatic, intralesional, and intracranial injection or infusion techniques. The nanoprobes can also be administered via catheters or through a needle to any tissue.

Dosing of nanoprobes will depend on a number of factors including the sensitivity of the detection system used, as well as a number of subject-related variables, including animal species, age, body weight, mode of administration, sex, diet, time of administration, and rate of excretion.

Below are some abbreviations that are used throughout the application: TO: thiazole orange; Dex-TO/DTO: dextran-thiazole orange conjugate; NA: nucleic acid; TLR: Toll-like receptor; FH: feraheme; NHS: N-hydroxysuccinimide; FPLC: Fast Protein Liquid Chromatography; FRI: fluorescence reflectance imaging; ROC: receiver operating characteristic; TTC: 2,3,5-triphenyltetrazolium chloride; AUC: area under the curve; DTPA: diethylene triamine pentaacetic acid; CNR: contrast to noise ratio; IR: ischemia-reperfusion; AV-750: Annexin V-near-infrared fluorochrome; AAR: area-at-risk; LPS: lipopolysaccharide; Dex: dextran; CCR2: C—C chemokine receptor type 2.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Examples

The following examples are illustrative and not limiting. All experiments and procedures were performed in accordance with the National Institutes of Health's "Guide for the Care and Use of Laboratory Animals" and were approved by the Massachusetts General Hospital Institutional Animal Care and Use Committee.

General Procedures

Continuous Wave Fluorescence Imaging

Heart slices sectioned along the short axis were exposed to Dex-TO or Dex-Cy5.5 and imaged on a commercial imaging system (IVIS Spectrum, PerkinElmer). Dex-TO fluorescence was detected with an excitation wavelength of 500 nm, emission wavelength of 540 nm and a 30-sec exposure time. Dex-Cy5.5 fluorescence was detected with an excitation wavelength of 675 nm, emission wavelength of 720 nm and a 30-sec exposure time. Microsphere fluorescence was detected with an excitation wavelength of 570 nm, emission wavelength of 620 nm and a 20-sec exposure time. AV-750 fluorescence was detected with an excitation wavelength of 745 nm, emission wavelength of 800 nm and a 30-sec exposure time. All images were acquired at a spatial resolution of 135 µm. Fluorescence intensity was quantified and analyzed in ImageJ (NIH, Bethesda Md.).

Molecular Magnetic Resonance Imaging (MRI)

Mice within 24 hours of permanent LCA ligation were injected with Gd-TO (0.1 mmol/kg ip). After 3 hours of probe circulation, Gd-TO enhanced MRI was performed on a 9.4 Tesla horizontal bore magnet (Biospec, Bruker, Billerica Mass.). Ti maps were acquired as described in Huang S, et al., Circ Cardiovasc Imaging. 2011; 4: 729-37. In addition, gradient echo cines were acquired in the short axis of the left ventricle using cardiorespiratory gating (SA Instruments, Stonybrook, N.Y.) and the following settings: Slice 1 mm, FOV 25×25 mm, Matrix 200×200, flip angle 30 degrees, 20 frames per RR interval, TE 1 ms, 4 averages. CNR and TBR were derived from these gradient echo cines, as described above.

Biodistribution

50 µCi of $^{111}$In-TO was injected intravenously into each mouse. The actual injected dose (ID) was determined by subtracting the residual radioactivity after injection from the dose prepared before injection. Tissues were harvested after 3 hours of tracer circulation time. Radioactivity in tissue was quantified as counts per minute (CPM), measured by a Wallac 1480 wizard gamma counter and Packard Tri-Carb liquid scintillation analyzer (Perkin Elmer). The tissue uptake was expressed as percentage of injected dose per gram of tissue (% ID/g).

Infarct Size Measurement

Excised hearts were sectioned axially into 1 mm thickness (McIlwain 800 Series, Vibratome, St Louis, Mo.) and stained with 2,3,5-triphenyltetrazolium chloride (TTC, from GFS Chemicals, Powell, Ohio) following the manufacturer's protocol. TTC images were acquired on a flatbed scanner (Hewlett Packard, Palo Alto, Calif.), and microsphere images were acquired on the IVIS spectrum. Image analysis was performed in ImageJ, with infarction size across the heart slices normalized to the area-at-risk (AAR).

Immunohistochemistry

Excised hearts were embedded in Optimal Cutting Temperature compound (OCT, from Thermo Fisher), and 10 µm short-axis cryo-sections were collected. Direct immunohistochemistry of CD68 was performed with anti-CD68 antibody conjugated to Alexa Fluor 647 fluorophore (Santa Cruz Biotechnology, Dallas, Tex.) per manufacturer's instructions. Diamidino-2-phenylindole (DAPI, from Thermo Fisher) staining was performed to visualize the nuclei. Microscopy was performed on a TISSUEFAXS system (TissueGnostics GmbH, Vienna, Austria), with a 40× objective lens (Zeiss), DAPI (for DAPI), GFP (for Gd-TO), and Alexa 647 (for CD68) filter settings. Images were acquired on a 12 bit CCD camera (Pixelink, Ottawa, Ontario, Canada), with the TissueFAXS image acquisition software, and analyzed in Image J (NIH).

Example 1. Synthesis 1.4 µmol of TO-NHS ester (synthesized according to the procedures in Garanger E, Hilderbrand S A, et al., Chem Commun (Camb). 2009: 4444-6) was prepared in 100 µl anhydrous DMSO, and added immediately to 5.4 mg of amino-dextran 40 kDa (Thermo Fisher Scientific, Waltham, Mass.) in 0.4 ml 1×DPBS. The reaction was incubated at 37° C. for 3 hours. After the solution had cooled down to room temperature, it was loaded on a PD-10 column, and eluted with 1 mM phosphate buffer (pH 7.0). The final product was collected and reconstituted into 1 mM phosphate buffer (2 ml). A light red powder was obtained after lyophilization. Dex-Cy5.5 was similarly synthesized by conjugating amino-dextran to Cy5.5-NHS ester (GE Healthcare, Little Chalfont, UK). A light blue powder was obtained after lyophilization.

Example 2. TO Valency Determination

Dex-TO solution was prepared at 2.2 µM (0.26 µmol isomaltose unit in 1 ml of 1×DPBS pH 7.4). 5 units of 400-800 units/mg lyophilized dextranase from *Penicillium* sp. (Sigma-Aldrich, St. Louis, Mo.), was prepared in 6 µl 1×DPBS, and added to the Dex-TO solution. Reaction kinetics were measured by UV spectra from 250 nm to 750 nm, on an Evolution 300 UV-Vis spectrometer (Thermo Scientific), and recorded at 0, 1, 2, and 20 hours after incubation at 37° C. The TO concentration was calculated according to the absorbance at 509 nm and an extinction coefficient of 63,000 $M^{-1}$ $cm^{-1}$ as described in Nygren J, et al. Biopolymers. 1998; 46: 39-51. An average of 2.8 TOs were present per nanoparticle Example 3. Dex-TO Size Measurement by FPLC The dynamically based molecular size (hydrodynamic volume) of Dextran-TO was determined by Fast Protein Liquid Chromatography (FPLC) using an AKTA Purifier 10 and Superdex 200 10/300GL column (GE Healthcare) with a running buffer of 0.05 M sodium phosphate, 0.15 M NaCl (0.1% Tween, pH 7.2) and flow rate of 0.8 ml/min. Gel filtration calibration standards (GE Healthcare) including conalbumin (C), ovalbumin (O), carbonic anhydrase (CA), RNase A (R), aprotinin (Apr) were run to obtain a standard curve, with size exclusion retention determined by Blue Dextran 2000. The partition coefficient (Kay) was calculated as $K_{av}=(V_e-V_0)/(V_t-V_0)$, where Ve=elution volume, $V_0$=void volume and Vt=total volume, and then plotted against the relative molecular weights ($M_r$) of the aforementioned standards. $M_r$ of Dex-TO was determined from the standard curve.

Calibration of Dex-TO (red) against known standards (black) revealed a particle diameter of 4.9 nm (FIG. 1G, H). In the presence of NAs, Dex-TO formed complexes up to 250 nm in diameter by light scattering (FIG. 1I).

Example 4. In Vitro Binding Assays

Bacterial Phage Lambda DNA (Sigma-Aldrich), CpG DNA (Enzo Life, Plymouth Meeting, Pa.), Torula yeast RNA (Sigma-Aldrich) were completely dissolved in Tris-acetate-EDTA (TAE) buffer (pH=8) by gentle inversion overnight at 4° C. Lambda DNA, CpG DNA, yeast RNA stock solutions were characterized by spectrophotometry to determine the concentration and purity. Total mouse heart RNA was extracted from C57Bl6 mouse hearts using TRI Reagent (Sigma-Aldrich) and characterized with a Nano-Drop spectrophotometer (Thermo Fisher) as described in Feng Y, Chen H, et al., J Biol Chem. 2015; 290: 26688-98.

To measure the fluorescence response in the presence of nucleic acid (NA), serial dilutions of the NA solutions with ratio of 1:3 were prepared in a Corning Costar 96-Well black clear-bottom plate (Thermo Fisher). 50 nM of fluorochrome equivalents, based on the common benzothiazole ring, were added to the NA-containing wells and incubated for 2 hours. Fluorescence was measured with the GloMax-Multi Detection System and snap-in fluorescent optical kits (Promega, Madison, Wis.). $EC_{50}$ was determined using the dose-response curve fitting function implemented in Prism (GraphPad, La Jolla, Calif.).

Example 5. Flow Cytometry

Cardiomyocyte line HL-1 cells were seeded on a 24-well plate at $1 \times 10^5$ cells/well. Cell necrosis/membrane rupture was induced with 50 µM final concentration of 2,3-Dimethoxy-1,4-naphthoquinone (DMNQ, from Sigma-Aldrich). Healthy control cells were treated with PBS. After 24 hours of incubation, the cells were trypsinized and co-stained with Dex-TO (300 nM) and Sytox Blue (1 µM) at 37° C. for 15 min. Sytox Blue is commercially available and can be purchased from Thermo Fischer Scientific (Waltham, Mass.). After washing with 1 ml of DPBS, cells were pelleted, resuspended in 300 µl of DPBS, and analyzed with a 4 laser LSRII system (BD Biosciences, Franklin Lakes, N.J.). Dex-TO was excited with the 488 nm solid state laser and emission detected with the 525/50 nm filter. Sytox was excited with the 405 nm violet laser and emission detected with the 450/50 nm filter. A compensation matrix was applied to correct for spectral overlap and signal spillover. Cytometry data was analyzed and scatterplots generated in Flowjo (Tree Star Inc., Ashland, Oreg.).

Characterization of the probe by flow cytometry showed that Dex-TO was excluded from healthy cells (FIG. 1C), but bound to necrotic cells with an affinity similar to commercial vital dyes such as Sytox Blue (FIG. 1D). Strong nuclear colocalization of Dex-TO and Sytox Blue was seen in necrotic cells (FIG. 1E). The multivalent nature of Dex-TO markedly enhanced its affinity for NA (FIG. 1F). The signal produced by TO, which is indicative of its binding to NA, was significantly higher with Dex-TO than with equivalent concentrations of monovalent TO (TO-PRO). No fluorescence increase was seen when either Dex-Cy5.5 or Cy5.5 was incubated with DNA.

Example 6. Confocal Microscopy

HL-1 cells were treated with 50 µM DMNQ and co-stained with Dex-TO (300 nM final concentration) and Sytox Blue (1 µM) for 15 min at room temperature. Confocal fluorescent images were acquired on a custom built 4-laser Zeiss Axio Observer Z1 inverted microscope (Carl Zeiss AG, Oberkochen, Germany) equipped with a confocal spinning-disk unit (CSU-X1) (Yokogawa, Musashino, Tokyo, Japan). Stained cells were observed using a 10× objective lens. Dex-TO was imaged with 425/20-25 nm excitation, 525/30 nm emission filter setting. Sytox Blue was imaged with 387/11-25 nm excitation, 440/40 nm emission filter setting. Images were recorded using an Evolve 512 electron-multiplying charge-coupled device (EMCCD) camera (Photometrics, Tucson, Ariz.), with Slidebook 5.1 Software (Intelligent Imaging Innovations (3i), Denver, Colo.), and processed in ImageJ (NIH).

Example 7. Dex-TO/DNA Aggregate Size Measurement

A Lambda DNA dilution series was prepared as above and incubated with 50 nM fluorochrome equivalents of Dex-TO for 2 hours at 37° C. Hydrodynamic size of the Dex-TO/DNA microaggregates was then measured by dynamic light scattering using a Zetasizer (Malvern Instruments, Marlboro, Mass.).

Example 8. $^{111}$In-TO-DTPA Synthesis and Characterization

In a 5 ml react vial, 1.663 mCi of $^{111}$InCl$_3$ stock solution (Nordion, Ottawa, Canada), diluted in 60 µl of 0.05 N HCl, was added to 0.8 mg (0.83 µmol) of TO-DTPA in 300 µl of 0.1 M acetic acid in a high purity water solution. The mixture was stirred at room temperature for 40 minutes. The labeling was validated by HPLC analysis of 10 µl of the reaction mixture, diluted into 500 µl of 0.1 M acetic acid in high purity water. HPLC was run on a Varian ProStar detector and delivery modules (Varian Medical Systems, Palo Alto, Calif.) with eluent A (0.1% TFA in water), and a gradient of 10-50% eluent B (0.1% TFA with 90% acetonitrile in 9.9% water) in 10 min, back to 10% B in 5 min and isocratic for 5 min, flow: 5 ml/min, 500 nm on a C18 column. Radiochemical yield (RCY) was >99%; Specific Activity was 2 mCi/µmol. Immediately before injection, the $^{111}$In-TO-DTPA solution was taken into a syringe, filtered through a 0.22 µm nylon filter, and washed with 2671 of sterilized 1×PBS.

Example 9. Myocardial Infarction

Myocardial Infarction was induced in adult female C57Bl6 mice (Jackson Laboratory, Bar Harbor, Me.) by permanent ligation of the left coronary artery (LCA) as described in Huang S, et al., Circ Cardiovasc Imaging. 2011; 4: 729-37. After 24 hours, a cohort of these mice (n=7) was co-injected intravenously with 10 nmol each of Dex-TO and Dex-Cy5.5 for fluorescence imaging. A second cohort was injected intravenously with 50 µCi of $^{111}$In-TO (n=6) to assess myocardial uptake and biodistribution, as described below. A separate group of mice was injected intraperitoneally with 0.1 mmol/kg Gd-TO (n=6) within 24 hours of the ligation for MR imaging. T1 maps of Gd-TO uptake in these mice have been reported in Huang S, et al., Circ Cardiovasc Imaging. 2011; 4: 729-37, but not TBR or CNR. CNR was calculated as $(\text{signal}_{infarct} - \text{signal}_{septum})/\text{sd}_{noise}$, where $\text{sd}_{noise}$ was the standard deviation of the noise. TBR was defined as $\text{signal}_{infarct}/\text{signal}_{septum}$.

Example 10. Myocardial Ischemia-Reperfusion

Ischemia-reperfusion (IR) injury was induced by transient occlusion of the LCA, followed by release of the suture to establish full reperfusion. The ECG was monitored to ensure that the ST segments remained elevated throughout the duration of occlusion. Mice core temperature was maintained at 38° C., and heart rate was maintained at 500 beats per minute. Reperfusion was confirmed visually and by resolution of the ST elevation. The released suture was left in place for subsequent religation and fluorescent microsphere injection, performed just prior to euthanasia, in order to delineate the area-at-risk (AAR).

To determine the kinetics of NA release in IR, mice fluorescence reflectance imaging were exposed to 35 minutes of transient occlusion of the LCA followed by reperfusion. Two hours prior to sacrifice, 10 nmol Dex-TO and 100 µl AV-750 (PerkinElmer, Waltham, Mass.) were co-injected into the tail vein. The mice were sacrificed at 2, 4, 6 or 24 hours after injury (n=6 per group). Hearts were sectioned into 1-mm short axial slices and imaged with fluorescence reflectance imaging (FRI). To determine whether the scavenging of NAs by Dex-TO exerted a protective effect in IR, a more aggressive model involving 45 minutes of LCA ligation was used. In one cohort of these mice (n=14) Dex-TO (10 nmol I.V.) was injected at the time of reperfusion, and again 4 hours later. A control cohort (n=14) underwent the identical protocol but was injected with 10 nmol of unconjugatd 40 kDa dextran. After 24 hours, half of the mice in each cohort (n=7) were re-anesthetized, the LCA was re-ligated, and the mice were injected with fluorescent microspheres 10 minutes prior to euthanasia. The excised hearts were embedded and cryosectioned for immunohistochemistry. The remaining mice (n=7 per cohort) were allowed to recover for 7 days at which time the LCA was re-ligated, followed immediately by microsphere injection and euthanasia. The excised hearts in these mice were sectioned axially into 1-mm slices for AAR assessment and TTC staining.

Mice Cohorts Imaged

A total of 11 cohorts of mice were imaged:
- A) Permanent occlusion of LCA—injection of Dex-TO, Dex-Cy5.5, and microspheres at 24 hours (n=7).
- B) Permanent occlusion of LCA—injection of Gd-TO within 24 hours (n=6).
- C) Permanent occlusion of LCA—injection of $^{111}$In-TO at 24 hours (n=6).
- D) 35-minute IR co-injected with Dex-TO, AV-750 and microspheres, in mice 2 hrs (n=6), 4 hrs (n=6), 6 hrs (n=6), and 24 hrs (n=6) after reperfusion.
- E) 45-minute IR injected with Dex-TO at reperfusion and at 4 hours—hearts sectioned for CD68 staining at 24 hours (n=7).
- F) 45-minute IR injected with control Dex at reperfusion and at 4 hours—hearts sectioned for CD68 staining at 24 hours (n=7).
- G) 45-minute IR injected with Dex-TO at reperfusion and at 4 hours—hearts sectioned for TTC staining of final infarct size at 7 days (n=7).
- H) 45-minute IR injected with control Dex at reperfusion and at 4 hours—hearts sectioned for TTC staining of final infarct size at 7 days (n=7).

The addition of NA to a solution of Dex-TO markedly prolonged its fluorescence lifetime, indicative of active binding (FIG. 2A). Fluorescence lifetime was also increased in the necrotic tissue of an infarcted mouse heart after the intravenous injection of Dex-TO, while no change was seen with the injection of Dex-Cy5.5 (FIG. 2B, C).

Figure 2E:
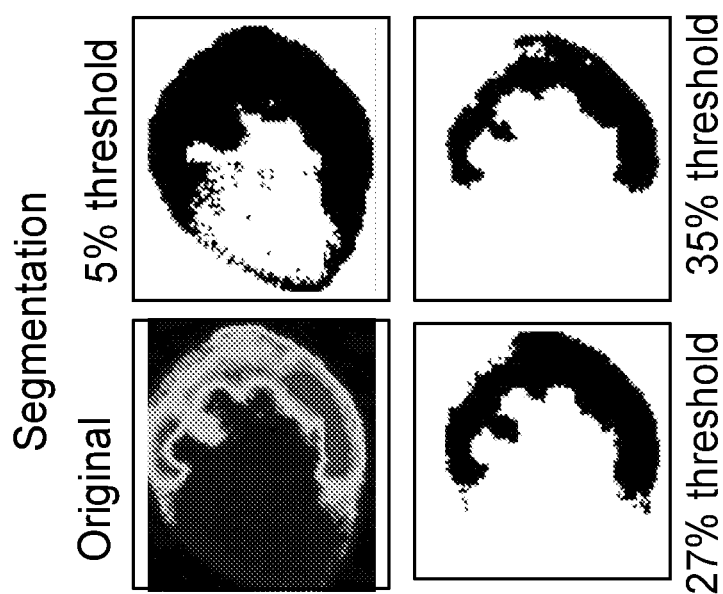
FIG. 2E is segmentation of Dex-TO fluorescence by thresholding based on the septal signal from the matching slice.

The detection of necrotic tissue with Dex-TO was systematically evaluated in acutely infarcted mice (n=7) with continuous wave FRI, due to its wide availability and ease of use. A strong correlation between Dex-TO uptake and infarct area by TTC staining was consistently seen (FIG. 2D). In contrast, no correlation was seen between infarction and Dex-Cy5.5 distribution. Receiver operating characteristic (ROC) analysis was performed to determine the optimal segmentation threshold for Dex-TO in the heart, with TTC staining serving as the gold standard. The thresholds tested were defined by the percent increase in signal intensity above the uninjured septum and ranged from 5-35% (FIG. 2E). ROC analysis revealed an optimal threshold of 27% and an area under the curve (AUC) of 0.88 (FIG. 2F).

Figure 3A:
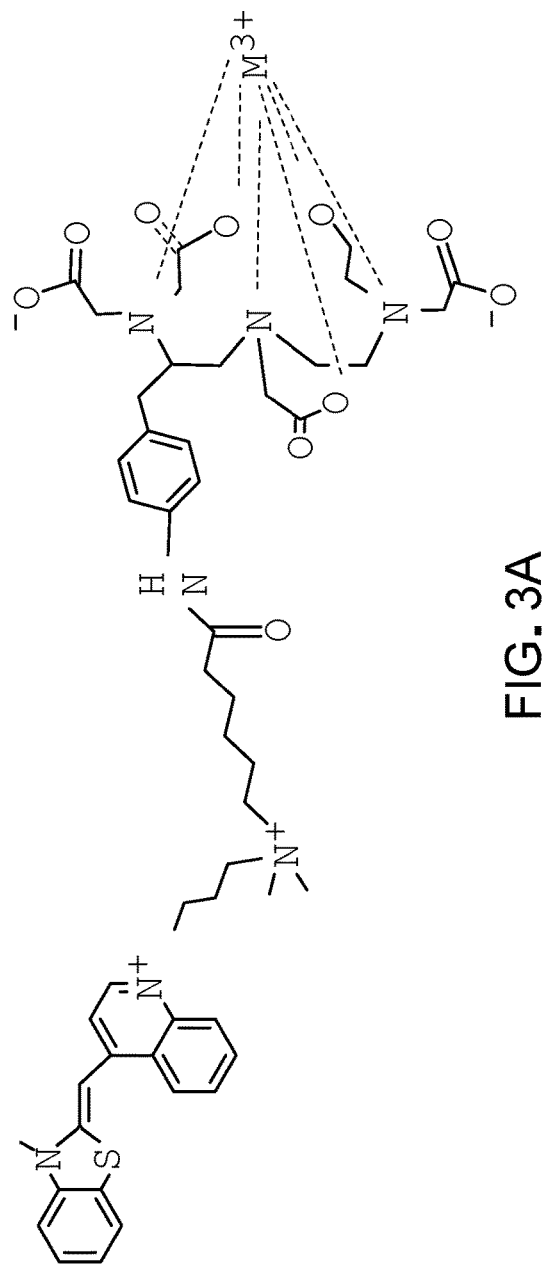
FIG. 3A is a structure of DTPA-TO chelates. Gd-TO is obtained when the metal (M) is $Gd^{3+}$, and $^{111}$In-TO is obtained with $^{111}$In$^{3+}$ chelation.
Figure 3B:
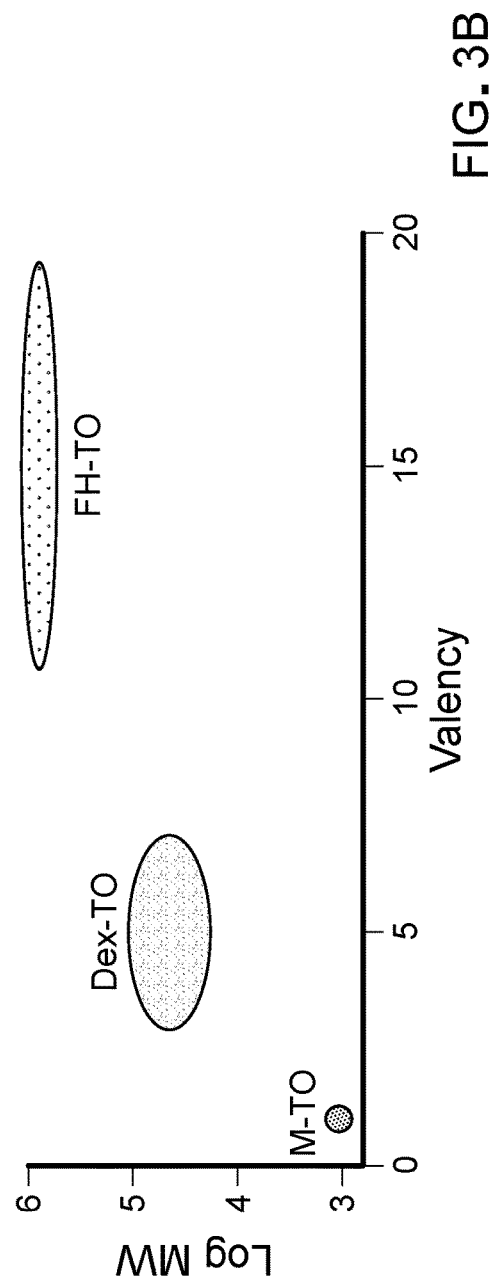
FIG. 3B is a graph showing that M-TOs have a low molecular weight and are monovalent; FH-TO forms a very large and highly multivalent nanoparticle; and Dex-TO is characterized by intermediate size and multivalency.
Figure 3D:
FIG. 3D is an inversion recovery gradient echo image of a mouse injected with Gd-TO 14 hours after infarction.
Figure 3C:
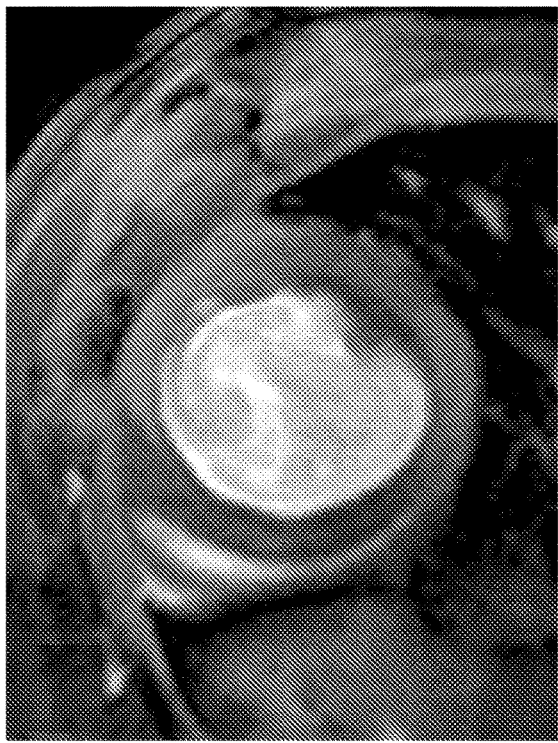
FIG. 3C is a gradient echo cine image of a mouse injected with Gd-TO 18 hours after infarction.

Further evaluation of Dex-TO as an imaging agent was performed by comparison with monovalent TO constructs, synthesized as shown in FIG. 3A. TO was conjugated to the metal binding chelate DTPA (diethylene triamine pentaacetic acid) as previously described (Garanger E, et al., Chem Commun (Camb). 2009: 4444-6). The uptake of two monovalent metal-TO chelates (Gd-TO and $^{111}$In-TO) was quantified in acutely infarcted mice (n=6 per group) and compared with Dex-TO (n=7). These agents form a spectrum of TO constructs (FIG. 3B) ranging from small molecules (Gd-TO, $^{111}$In-TO) and small nanoparticles (Dex-TO), to large nanoparticles (FH-TO). A mouse injected with Gd-TO and imaged with a conventional gradient echo cine 18 hours after injury is shown in FIG. 3C. The contrast generated by this sequence is moderate. In comparison, marked contrast was produced in mice imaged with inversion recovery gradient echo within 24 hours of injury (FIG. 3D).

Figure 3E:
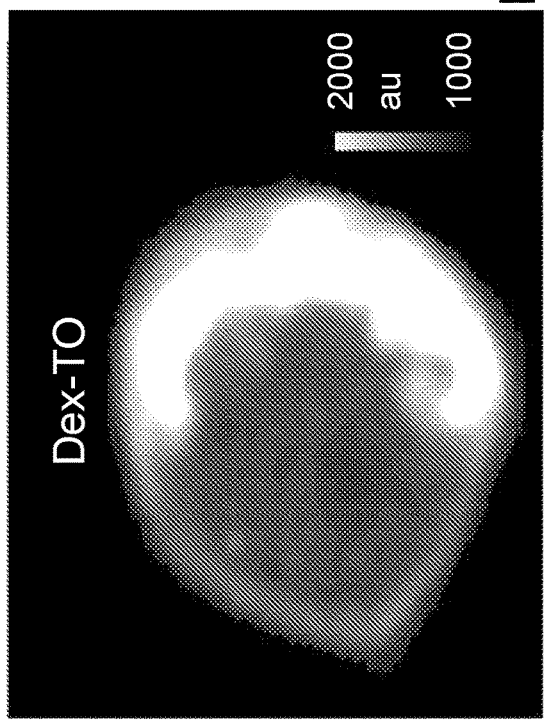
FIG. 3E is Dex-TO fluorescence of a heart 24 hours after infarction.
Figure 3F:
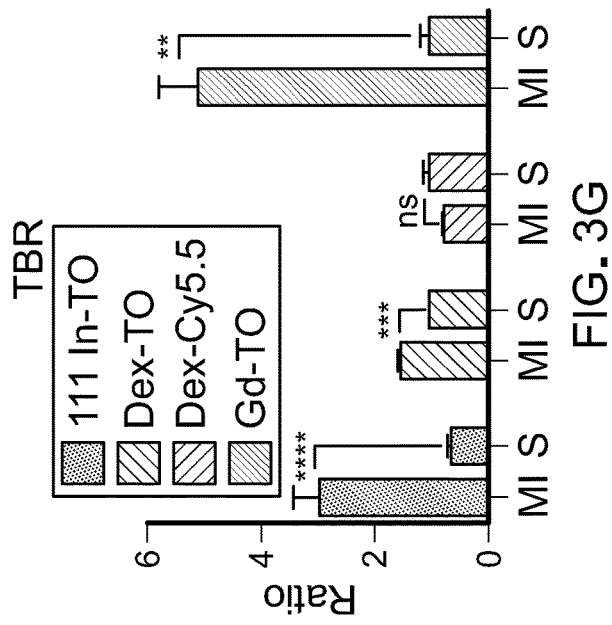
FIG. 3F is a graph showing the biodistribution of $^{111}$In-TO shows a 5-fold higher uptake in infarcted versus remote (septal) myocardium.
Figure 3G:
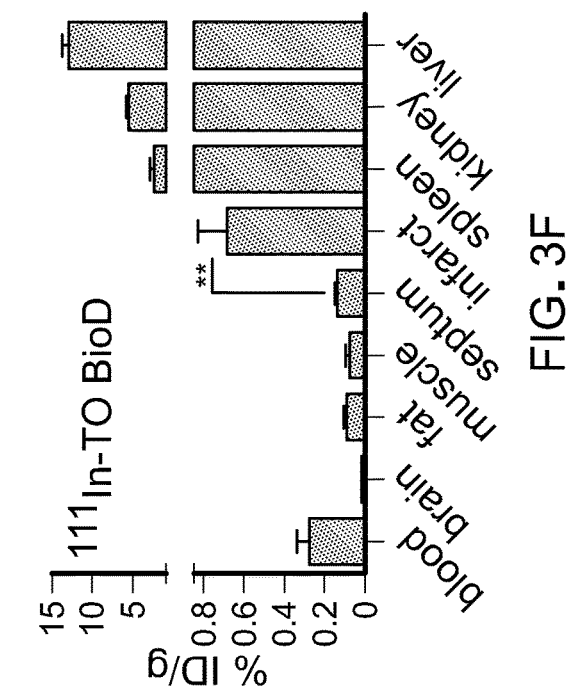
FIG. 3G and FIG. 3H are graphs that show the target to background ratio in the infarct (MI) is significantly increased with all TO probes.
Figure 3H:
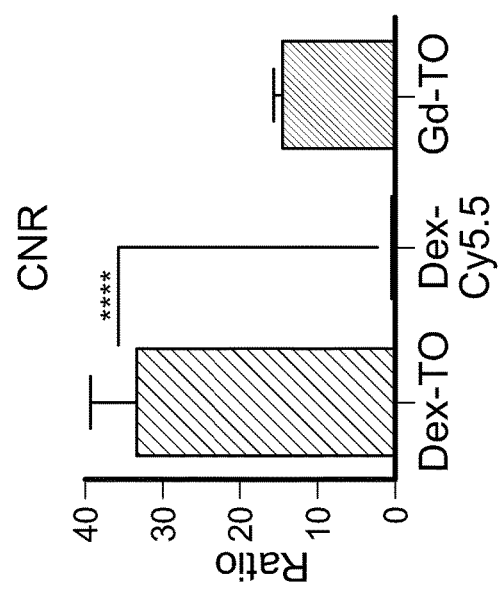

FRI of Dex-TO also produced strong contrast (FIG. 3E), but unlike inversion recovery gradient echo, the signal in the septum was not nulled. The biodistribution of $^{111}$In-TO showed significantly higher uptake in the infarct than the uninjured septum. The target to background ratios of $^{111}$In-TO ($2.9\pm1.3$ infarct vs $0.6\pm0.3$ septum, p<0.0001) and Dex-TO ($1.5\pm0.2$ infarct vs $1.0\pm0.1$ septum, p<0.001) were both significantly elevated (FIG. 3G). Likewise, both Gd-TO ($14.2\pm3.5$) and Dex-TO ($33.1\pm16.1$ vs 0 for Dex-Cy5.5, p<0.0001) generated a high contrast-to-noise ratio (CNR) between the infarct and the septum (FIG. 3H). The tissue contrast generated by Dex-TO thus compared very favorably with Gd-TO and $^{111}$In-TO.

Figure 4A:
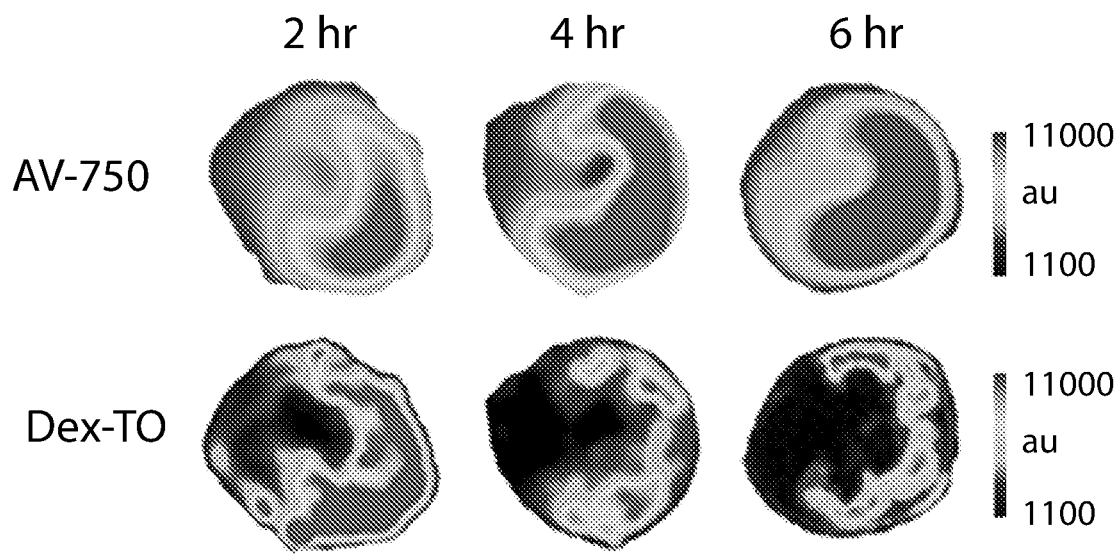
FIG. 4A are images of annexin V (AV-750; top line) and Dex-TO (bottom line) accumulation in the area-at-risk (AAR) 2, 4 and 6 hours after reperfusion.
Figure 4B:
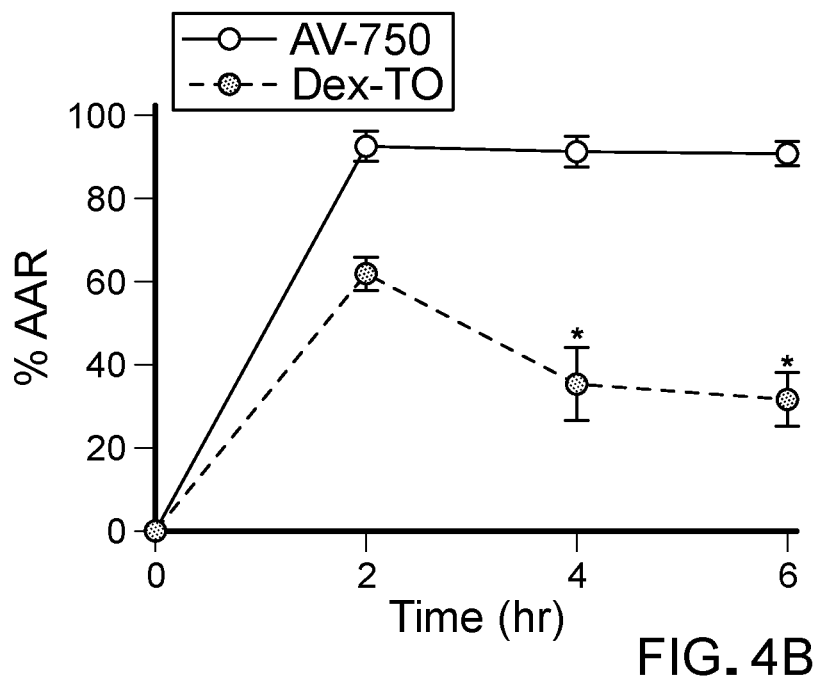
FIG. 4B is a graph showing Dex-TO accumulates widely in the AAR at 2 hours but undergoes a significant degree of washout between 2-4 hours. AV-750 is represented by the top line and Dex-TO is represented by the bottom line.
Figure 4C:
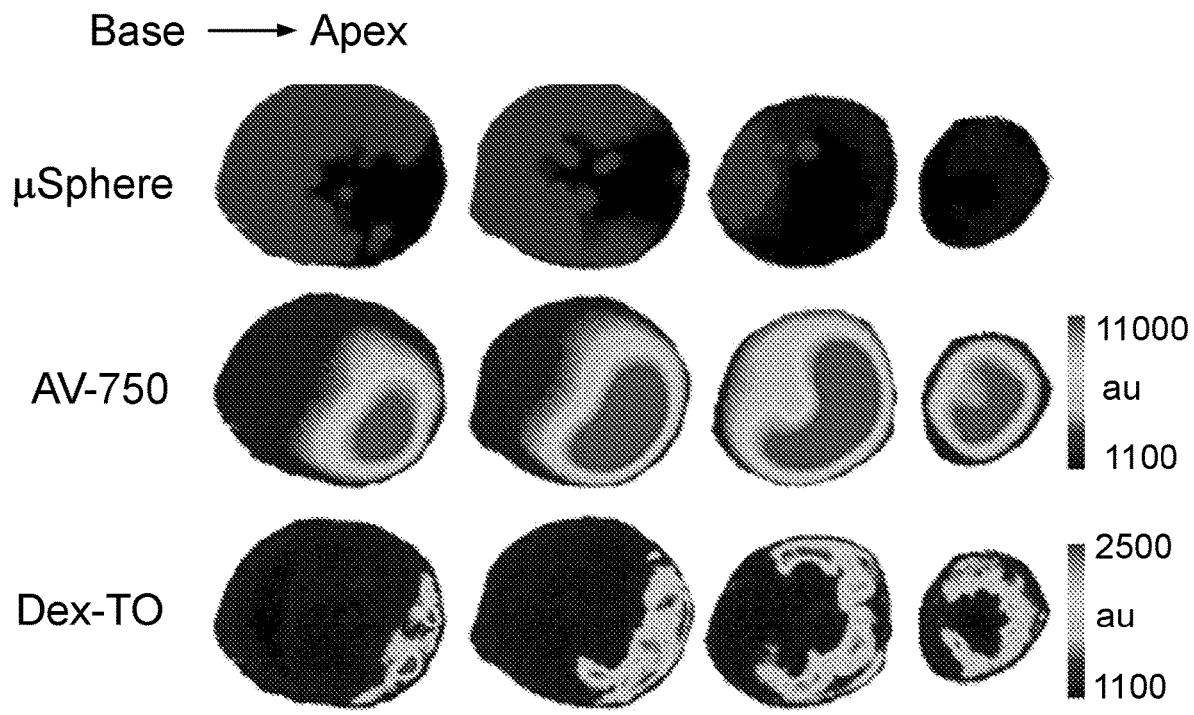
FIG. 4C are images of a heart subjected to ischemia-reperfusion at 6 hours.
Figure 4D:
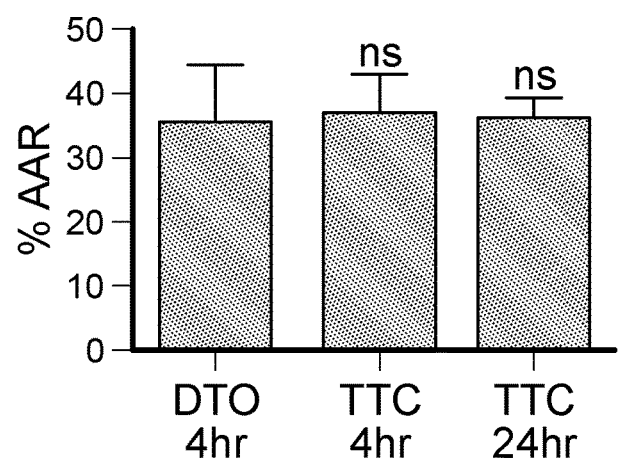
FIG. 4D is a graph showing the infarct size after 35 minutes of ischemia-reperfusion determined by Dex-TO (DTO) injection, TTC staining at 4 hours and TTC at 24 hours.

The kinetics of NA release in myocardial ischemia-reperfusion (IR) by Dex-TO fluorescence was characterized. Near-infrared Annexin V (AV-750) was co-injected to detect cardiomyocyte apoptosis. Fluorescent microspheres were injected prior to reperfusion to define the area-at-risk (AAR). Mice were euthanized 2, 4, 6 or 24 hours after injury (n=6 per group). As shown in FIG. 4A, the distribution of NA within the AAR was highly dynamic during the first 6 hours of reperfusion. At 2 hours the distribution of released NA correlated strongly with the distribution of apoptosis (AV-750) and filled much of the AAR. Thereafter, substantial washout of NA was seen, and by 4 hours the extent of myocardium positive for NA release was far smaller than the extent of apoptosis in the AAR (FIG. 4B, C). The washout of released NAs from the AAR was largely complete within 4 hours, and the distribution of Dex-TO at this time resembled final infarct size (FIG. 4D).

Example 11. Fluorescence Lifetime Imaging

Dex-TO (300 nM final concentration) with or without Lambda DNA, and a control sample containing buffer only were incubated at 37° C., for 2 hours before imaging. In addition, mice after 24 hours of permanent LCA ligation were co-injected intravenously with Dex-TO and Dex-Cy5.5 (10 nmol each), which were allowed to circulate for 2 hours prior to euthanasia. The hearts were then harvested and sectioned into 1-mm axial slices for fluorescence lifetime imaging and TTC staining. Time resolved imaging of heart slices was performed with a custom-built imaging system described in detail previously (Kumar A T, et al., IEEE Trans Med Imaging. 2008; 27: 1152-63). Briefly, fluorescence was excited with the direct output of a pulsed broadband (480 to 850 nm) Mai Tai titanium sapphire laser with 80 MHz repetition rate (Spectra-physics, Santa Clara, Calif.), photonic crystal fiber (Thorlabs, Newton, N.J.) filtered through either the 495±25 nm (Dex-TO) or 650/40 nm (Dex-Cy5.5) filter. The resulting fluorescence emission was detected with either a 529±25 nm filter (Dex-TO), or a 700-nm long pass filter (Dex-Cy5.5), both coupled to an intensified 12-bit cooled CCD camera with a 300-500 ps gate width, 600 V gain, 150 ps steps and 4×4 hardware binning (LaVision GmbH, Goettingen, Germany). The gated intensified CCD camera provided 200 ps time resolution with a 2×2 cm$^2$ field-of-view. Excitation powers were 50 µW/cm$^2$ at both 495 and 650 nm, and camera integration times ranged from 100 ms to 3 s.

Example 12. Macrophage Cytokine Production-Multiplexed Cytokine Assay

Bone marrow cells were harvested from the tibias and femurs of C57Bl6 mice and seeded in a 96-well plate at 2×10$^5$ cells/well, as previously described (Feng Y, et al., J Biol Chem. 2015; 290: 26688-98). Cells were cultured in supplemented RPMI 1640 medium in the presence of 10 ng/ml macrophage colony-stimulating factor (R&D systems, Minneapolis, Minn.) to induce differentiation into bone marrow derived macrophages (BMDMs). On day 5, the BMDMs were exposed to a variety of stimuli including CpG DNA, purified mouse heart RNA, and Lipopolysaccharides (LPS) from *Escherichia coli* (Sigma-Aldrich). The BMDMs were exposed to the stimuli in culture. After 24 hrs, cytokine production in the culture medium was measured.

The culture media from the stimulated BMDMs were collected and stored at −80° C. for cytokine protein measurements. CXCL2 (chemokine ligand 2) levels were measured with a commercial ELISA kit (R&D systems, Minneapolis, Minn.) following manufacturer's instructions. TNF-alpha, IL-6 and IL-10 concentrations were determined using a fluorescent bead-based multiplex immunoassay (Luminex, Austin, Tex.). Briefly, an antibody for each cytokine was covalently immobilized to a set of fluorescent microspheres by the manufacturer (Millipore, Billerica, Mass.). After overnight incubation, cytokines bound on the surface of the microspheres were detected by the mixture of biotinylated antibodies. After binding of streptavidin-phycoerythrin conjugates, the reporter fluorescent signal was measured with a Luminex 200 reader (Luminex). Final cytokine concentrations were calculated based on a standard curve constructed for each experiment. Cytokine production by DNA, RNA and LPS was measured under several conditions. To determine whether Dex-TO would decrease cytokine production, the nanoprobe was added to the culture medium to produce concentrations of 10 µM or 100 µM of Dex-TO. Control conditions included adding 10 µM of Dextran, 100 µM of Dextran or PBS to the medium.

Dex-TO was first exposed to a panel of pro-inflammatory NAs (FIG. 5A-D) to confirm its affinity and determine the EC$_{50}$. Mouse heart RNA had an EC$_{50}$ of 6.5 µg/ml, while yeast RNA had an EC$_{50}$ of 4.1 µg/ml. CpG DNA, a synthetic ligand for Toll-like receptor 9 (TLR-9) had an EC$_{50}$ of 100 nM (0.2 µg/ml), while bacterial DNA had an EC$_{50}$ of 0.06 nM (60 pM, 0.2 µg/ml). The bone-marrow derived mouse macrophages were exposed to RNA, DNA, and lipopolysaccharide (LPS). This stimulated the production of the proinflammatory cytokines TNF-alpha, CXCL2 and IL-6 by the activated macrophages, but no impact on the anti-inflammatory cytokine IL-10 (FIG. 5E) was seen.

Figure 5E:
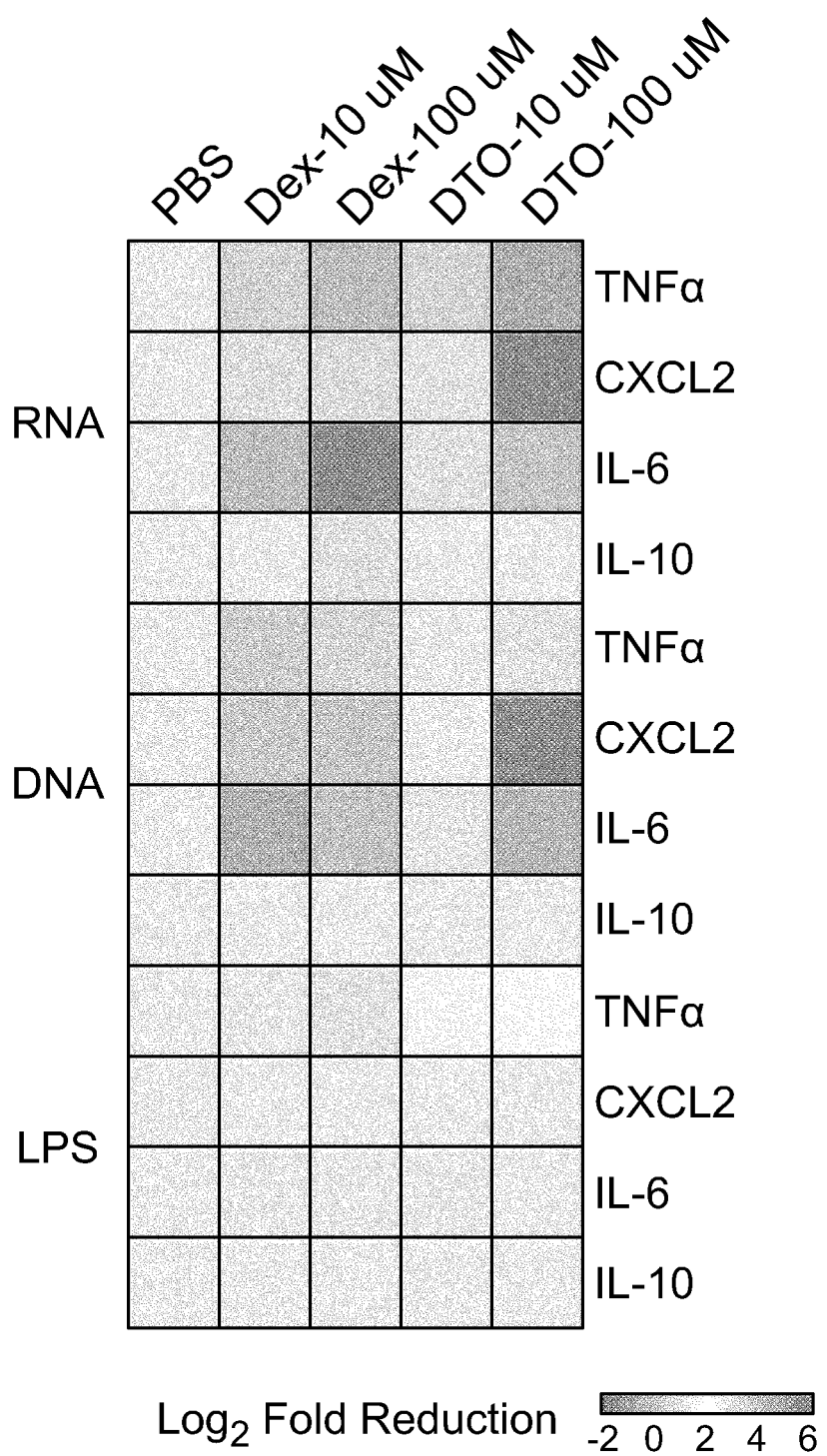
FIG. 5E is a plot showing Dex-TO (DTO) reduces the production of TNF-alpha, CXCL2 and IL-6 by activated macrophages exposed to mouse heart RNA or CpG DNA in a dose dependent fashion.

The addition of 10 µM Dex-TO (DTO) to the solution containing the NA-exposed macrophages reduced the production of TNF-alpha, CXCL2, and IL-6 by the macrophages significantly. A dose of 100 µM of Dex-TO produced a 64-fold reduction in cytokine production (FIG. 5E). Dex-TO did not reduce IL-10 production or LPS-induced cytokine production. This suggests that the anti-inflammatory effect of Dex-TO was mediated via specific scavenging of NA and interference with NA mediated stimulation of TLRs. Control amino-dextran (without TO) caused an unexpected, but mild, increase in cytokine production. This is consistent with prior reports of immune stimulation by dextran in mice (Coutinho A, et al., Scand J Immunol. 1974; 3: 321-8; Duplancic B, et al., Eur J Pharmacol. 2014; 727: 75-9; Blanckmeister C A, et al., J Leukoc Biol. 1985; 37: 209-19). The same amino-dextran preparation was used to synthesize Dex-TO, making the large reductions in cytokine production produced by Dex-TO even more noteworthy.

Figure 6F:
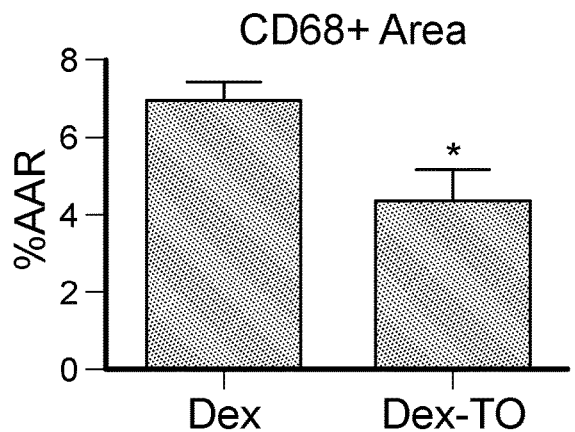
FIG. 6F and FIG. 6G are graphs showing Dex-TO significantly reduced the CD68 positive portion of the AAR by 37% and CD68 fluorescence by 26%.
Figure 6G:
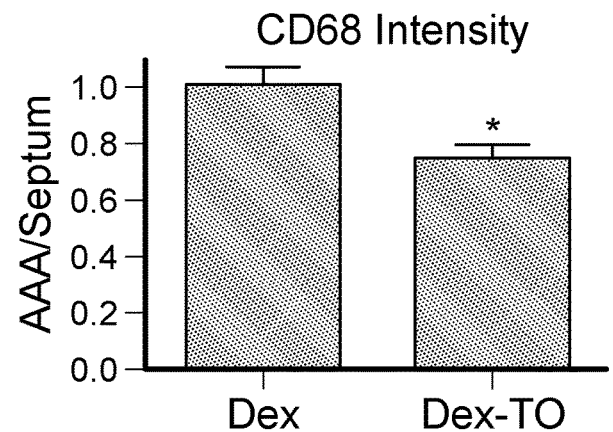
Figure 6H:
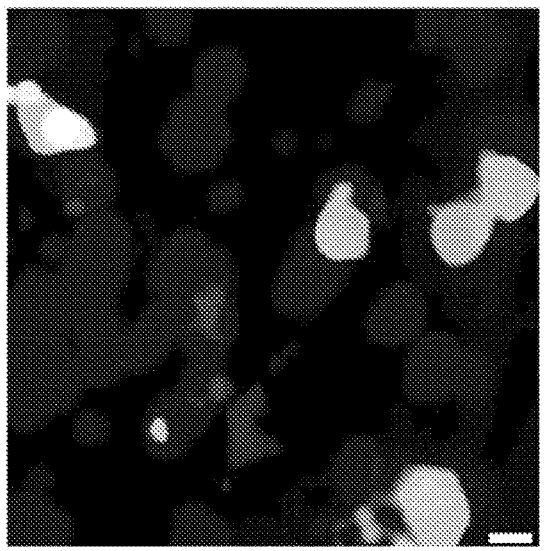
FIG. 6H and FIG. 6I are fluorescence microscopy and chart, respectively, of a Dex-TO treated heart co-stained with CD68 and DAPI.
Figure 6I:
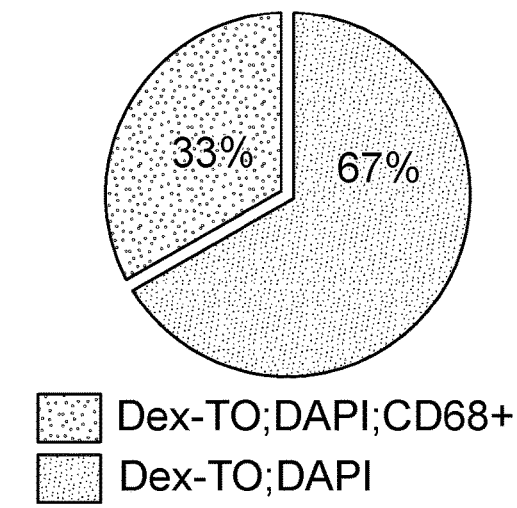

After 45-min of ischemia, Dex-TO (10 nmol) was injected intravenously at the onset of reperfusion and again 4 hours later (FIG. 6A). Control mice with IR were injected with an equivalent amount of Dextran (Dex). Half the mice were used to study the impact of Dex-TO injection on myocardial macrophage infiltration at 24 hours. The left coronary artery in these mice was religated at 24 hours and fluorescent microspheres were injected to delineate the AAR. The mice (7 control and 7 Dex-TO treated) were then euthanized and the hearts were sectioned and stained with CD68, a surface marker for infiltrating leukocytes (predominantly macrophages at 24 hours) that remains elevated in both mice and humans with healing myocardial infarcts Heidt T, et al., Circ Res. 2014; 115: 284-95; Lee W W, et al., J Am Coll Cardiol. 2012; 59: 153-63). The infiltration of CD68 positive cells was significantly reduced in the mice injected with Dex-TO (FIG. 6B, G). High magnification microscopy of a Dex-TO treated heart is shown in FIG. 6H and the results are summarized in FIG. 6I. All Dex-TO positive foci colocalized with DAPI, while only 33% colocalized with CD68 positive cells. This suggests that the attraction of CD68 positive cells to released NAs was attenuated by Dex-TO.

Figure 6J:
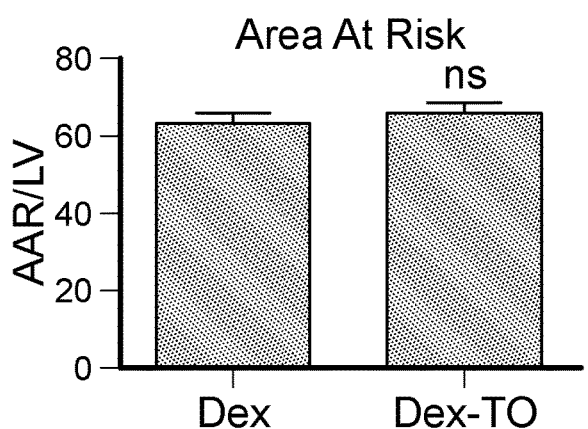
FIG. 6J is a graph that shows there is no difference in the AAR between the Dex-TO and Dex cohorts.
Figure 6K:
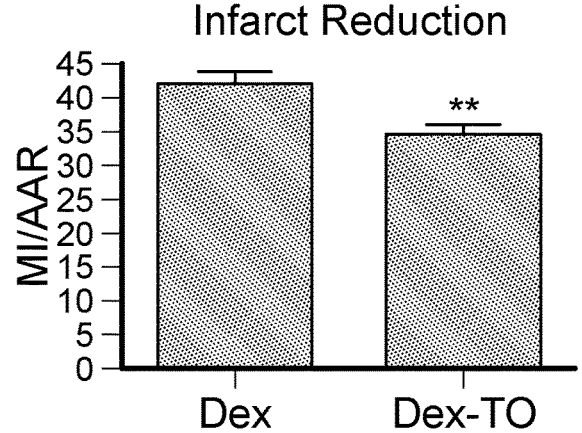
FIG. 6K is a graph that shows there is significant 18% reduction in infarct size was seen on day 7 with Dex-TO treatment. * $p<0.05$, ** $p<0.01$.

The impact of Dex-TO on final infarct size was tested in 14 mice (7 control and 7 Dex-TO treated). The treatment regimen on day 1 was as above, and infarct size was assessed on day 7 (FIG. 6A). The left coronary artery was religated on day 7, fluorescent microspheres were injected to delineate the AAR, and infarct size was assessed with TTC. No significant difference was seen in the AAR between the two groups (FIG. 6J). However, Dex-TO treatment significantly reduced infarct size by 18% (FIG. 6K). Taken together, these results show that Dex-TO given within 4 hours of reperfusion injury is anti-inflammatory and cardio-protective.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A nucleic acid binding nanoprobe having structure of Formula I:

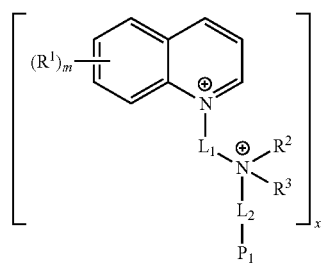

or a pharmaceutically acceptable salt thereof;
wherein:
each $L_1$ is independently $C_{2-20}$ alkylene;
each $L_2$ is independently $C_{2-20}$ alkylene, wherein any of the carbons in the $C_{2-20}$ alkylene chain is optionally replaced with $C(O)$, $O$, $S$, $S(O)$, $S(O)_2$, $NR^{a1}$ $NR^{b1}C(O)$, or a triazole;
$P_1$ is a polysaccharide;
each $R^1$ is independently $(CH)_t$-5-10 membered heteroaryl, $(CH)_u$-5-10 membered heterocycloalkyl, $C_{6-10}$ aryl, or $NR^{a2}R^{b2}$; wherein each 5-10 membered heteroaryl and 5-10 membered heterocycloalkyl has at least one ring-forming carbon atom and 1, 2, 3, or 4 ring-forming N or S atoms; and wherein the $C_{6-10}$ aryl, 5-10 membered heteroaryl, and 5-10 membered heterocycloalkyl are each optionally substituted with 1, 2, or 3 substituents independently selected from $C_{1-6}$ alkyl, $NH_2$, $NH(C_{1-6}$ alkyl), and $N(C_{1-6}$ alkyl$)_2$;
or two $R^1$ adjacent to each other and together with the carbon atoms to which they are attached form an $C_{6-10}$ aryl; wherein the $C_{6-10}$ aryl is optionally substituted with 1, 2, 3, or 4 substituents independently selected from $C_{1-6}$ alkyl, $NH_2$, $NH(C_{1-6}$ alkyl), and $N(C_{1-6}$ alkyl$)_2$;
$R^2$ and $R^3$ are independently selected from H and $C_{1-6}$ alkyl;
each $R^{a1}$, $R^{b1}$, $R^{a2}$, and $R^{b2}$ is independently selected from H and $C_{1-6}$ alkyl;
m is 1, 2, 3, or 4;
t is 1, 2, 3, 4, 5, or 6;
u is 1, 2, 3, 4, 5, or 6;
x is about 2 to about 20, and
wherein the nanoprobe does not comprise a metal.

2. The nanoprobe of claim 1, wherein each $L_1$ is independently $C_{3-6}$ alkylene.

3. The nanoprobe of claim 1, wherein each $L_2$ is independently $C_{10-20}$ alkylene, wherein any of the carbons in the $C_{10-20}$ alkylene chain is optionally replaced with $C(O)$, $O$, $NR^{a1}$ $NR^{b1}C(O)$, or a triazole.

4. The nanoprobe of claim 1, wherein the polysaccharide is about 5 to about 120 kDa in mass.

5. The nanoprobe of claim 1, wherein the polysaccharide is dextran, pullulan, dextrin, hydroxyethyl starch.

6. The nanoprobe of claim 1, wherein each $R^1$ is independently $(CH)_t$-5-10 membered heteroaryl or $(CH)_u$-5-10 membered heterocycloalkyl.

7. The nanoprobe of claim 1, wherein $R^2$ and $R^3$ are $C_{1-6}$ alkyl.

8. The nanoprobe of claim 1, wherein m is 1 or 2.

9. The nanoprobe of claim 1, wherein x is 3, 4, 5, 6, 7, or 8.

10. The nanoprobe of claim 1, wherein the moiety

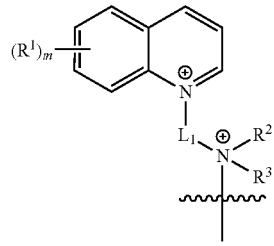

is selected from:

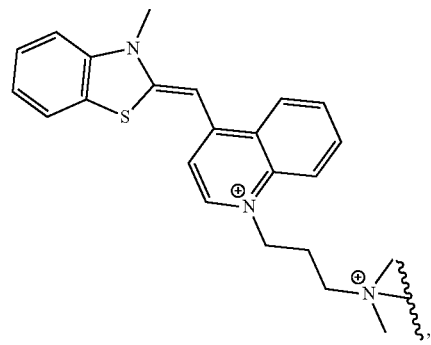

,

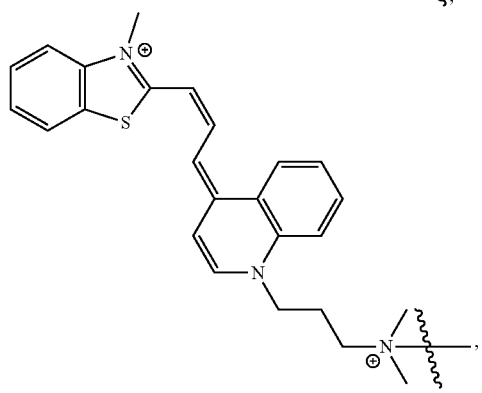

,

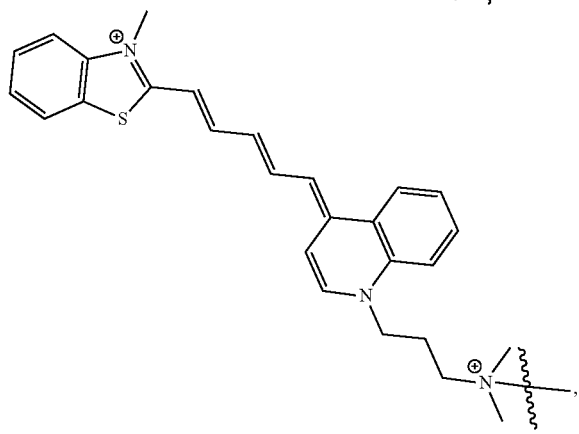

,

-continued

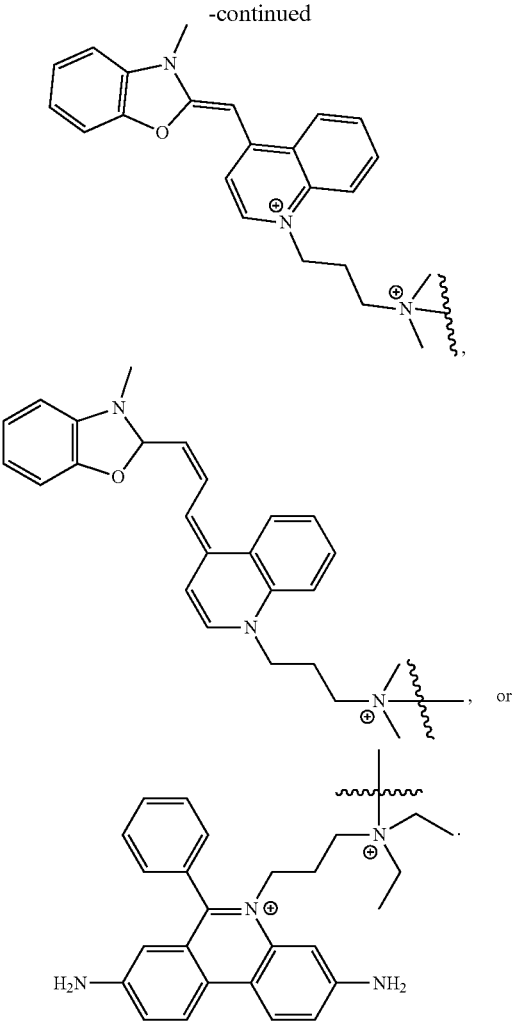

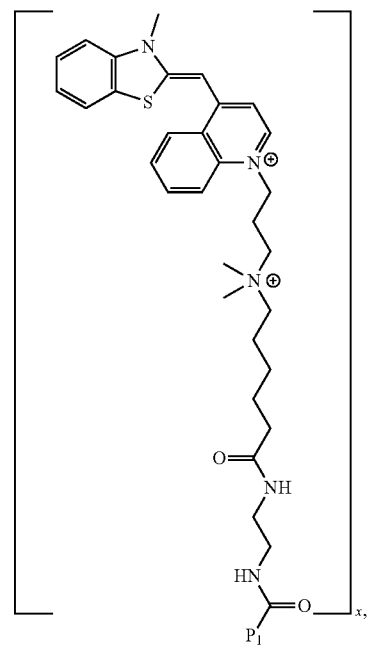

11. The nanoprobe of claim 1, wherein the nanoprobe is or a pharmaceutically acceptable salt thereof;

wherein x is 2 or 3; $P_1$ is dextran, wherein the dextran is about 40 kDa in mass.

12. The nanoprobe of claim 1, wherein x is about 2 to about 10.

13. The nanoprobe of claim 1, wherein the nanoprobe is about 40 to about 1000 kDa in mass.

14. The nanoprobe of claim 1, wherein the nanoprobe is about 4 to about 10 nm in diameter.

* * * * *

UNITED STATES PATENT AND TRADEMARK OFFICE
CERTIFICATE OF CORRECTION

| | | |
|---|---|---|
| PATENT NO. | : 11,779,661 B2 | Page 1 of 1 |
| APPLICATION NO. | : 16/348572 | |
| DATED | : October 10, 2023 | |
| INVENTOR(S) | : David Sosnovik, Lee Josephson and Howard Chen | |

It is certified that error appears in the above-identified patent and that said Letters Patent is hereby corrected as shown below:

In the Claims

In Column 31, Line 6, Claim 1, after "having" insert -- a --

In Column 31, Line 60, Claim 3, after "NR$^{a1}$" insert -- , --

In Column 31, Line 64, Claim 5, after "dextrin," insert -- or --

In Column 33, Line 27 (approx.), Claim 10, replace "or" with -- and --

Signed and Sealed this
Second Day of January, 2024

Katherine Kelly Vidal
*Director of the United States Patent and Trademark Office*